United States Patent [19]
Jenkins et al.

[11] 3,985,133
[45] Oct. 12, 1976

[54] IV PUMP

[75] Inventors: Jon Arthur Jenkins, Rancho Santa Fe; Orris H. Flatten, Yorba Linda; Oscar E. Hyman, Santa Ana, all of Calif.

[73] Assignee: Imed Corporation, San Diego, Calif.

[22] Filed: May 28, 1974

[21] Appl. No.: 473,901

[52] U.S. Cl. .................... 128/214 F; 128/DIG. 12; 128/214 E; 417/415
[51] Int. Cl.² ........................................ A61M 5/20
[58] Field of Search ......... 128/214 R, 214 B, 214 E, 128/214 F, 214.2, 203, 234, 218 A, 218 G, 273, DIG. 1, DIG. 12, DIG. 13; 417/415, 12, 419, 519, 360; 222/59, 70

[56] References Cited
UNITED STATES PATENTS

| | | | |
|---|---|---|---|
| 1,481,794 | 1/1924 | Dupin | 128/214 B |
| 1,948,388 | 2/1934 | Liberson | 128/234 |
| 2,602,446 | 7/1952 | Glass et al. | 128/218 A |
| 2,835,252 | 5/1958 | Mauchel | 128/214 E |
| 3,091,239 | 5/1963 | Moeller | 128/214 F |
| 3,335,724 | 8/1967 | Gienapp | 128/218 A |
| 3,447,479 | 6/1969 | Rosenberg | 128/234 X |
| 3,456,648 | 7/1969 | Lee et al. | 128/214 E |
| 3,701,345 | 10/1972 | Heilman et al. | 128/218 AX |
| 3,731,679 | 5/1973 | Wilhelmson et al. | 128/214 F |
| 3,736,930 | 6/1973 | Georgi | 128/214 E |
| 3,737,251 | 6/1973 | Berman et al. | 417/12 |
| 3,739,943 | 6/1973 | Wilhelmson et al. | 222/59 |
| 3,841,799 | 10/1974 | Spinosa et al. | 417/477 |
| 3,858,581 | 1/1975 | Kamen | 128/218 A |
| 3,901,231 | 8/1975 | Olson | 128/214 F |

*Primary Examiner*—Dalton L. Truluck
*Attorney, Agent, or Firm*—Ellsworth R. Roston

[57] ABSTRACT

A volumetric infusion pump for intravenous administration of fluid to a patient, including a volumetric cassette for receiving fluid from an IV fluid container and for pumping such fluid at a controlled rate using an IV administration set until a predetermined volume of fluid has been infused into the patient. The volumetric cassette contains, when filled, a predetermined volume of fluid. The cassette, when coupled to a driving mechanism in the pump, provides for the fluid to be pumped from the cassette at a predetermined rate. Once the cassette chamber has been at least partially emptied a predetermined amount by the operation of the pump, the volumetric chamber of the cassette is rapidly filled and the pumping continues with such emptying and filling of the cassette chamber alternately occurring until the predetermined volume of fluid has been pumped. The cassette is of a syringe type having a chamber and a plunger piston and the stroke of the plunger is controlled by the driving mechanism of the pump. A plurality of alarm mechanisms provide safety in the operation of the pump and provide output indications to give the operator a diagnosis of the reason that the pump has been alarmed. These alarms include air-in-line, low battery, occlusion of the line, and infusion complete.

62 Claims, 24 Drawing Figures

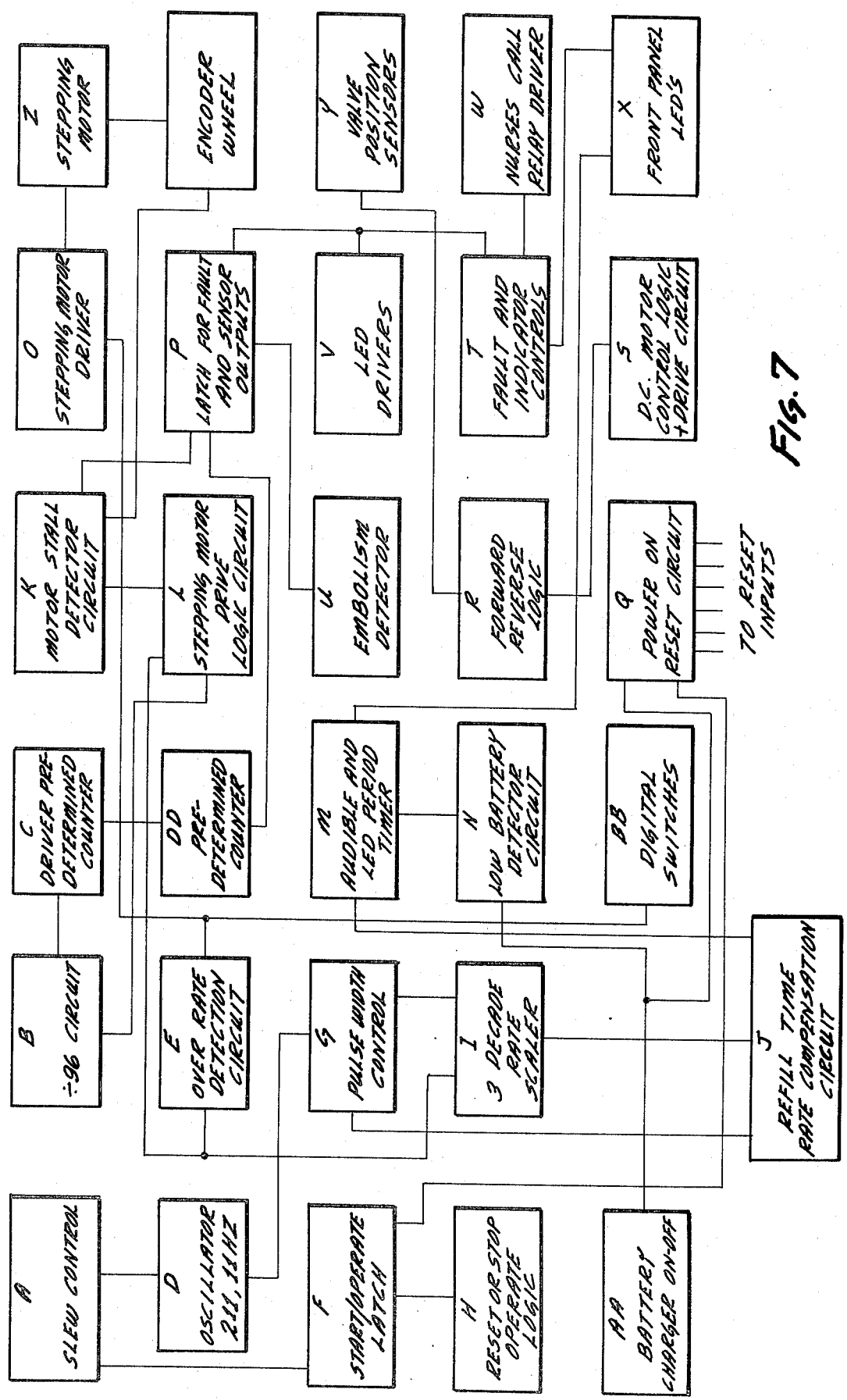

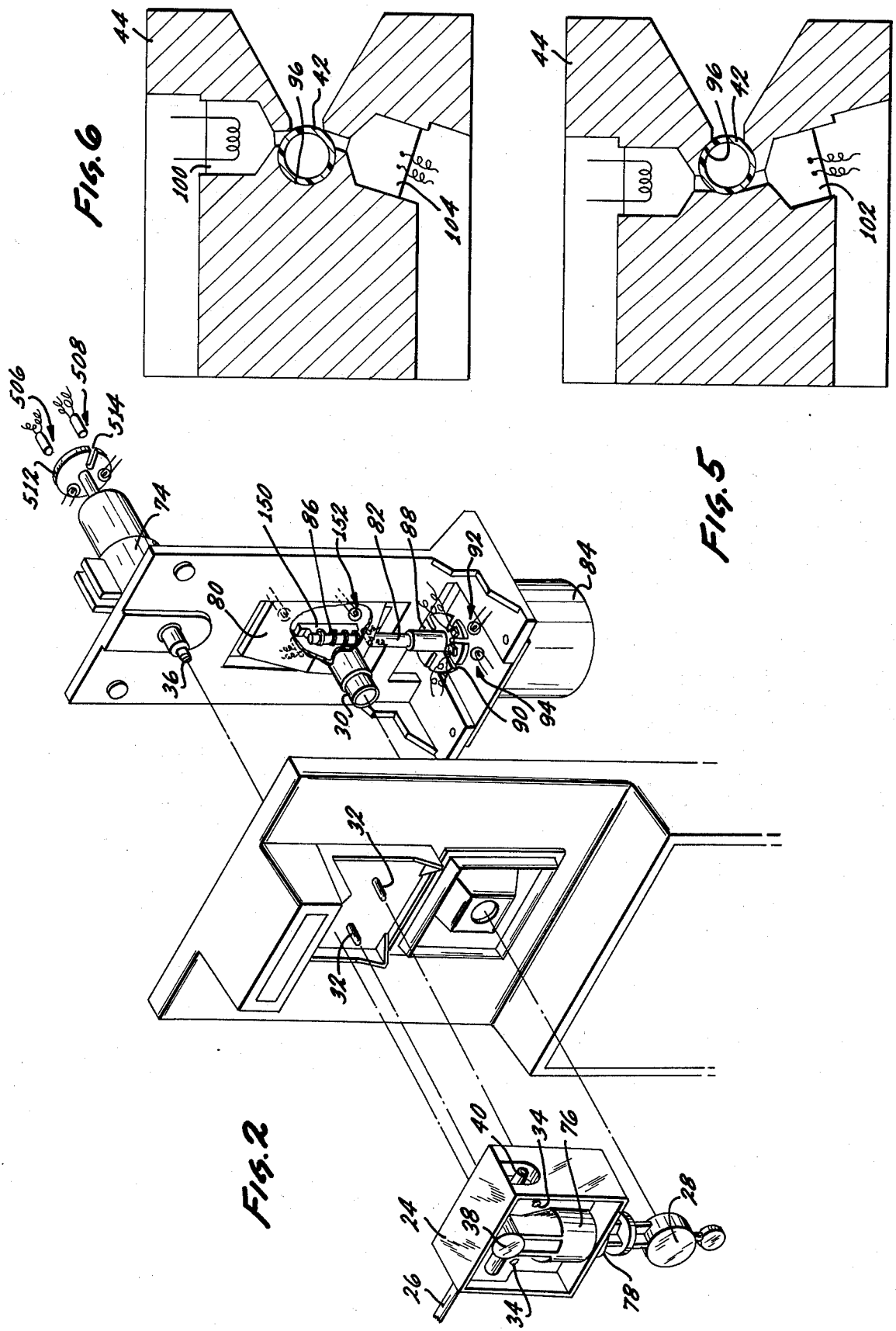

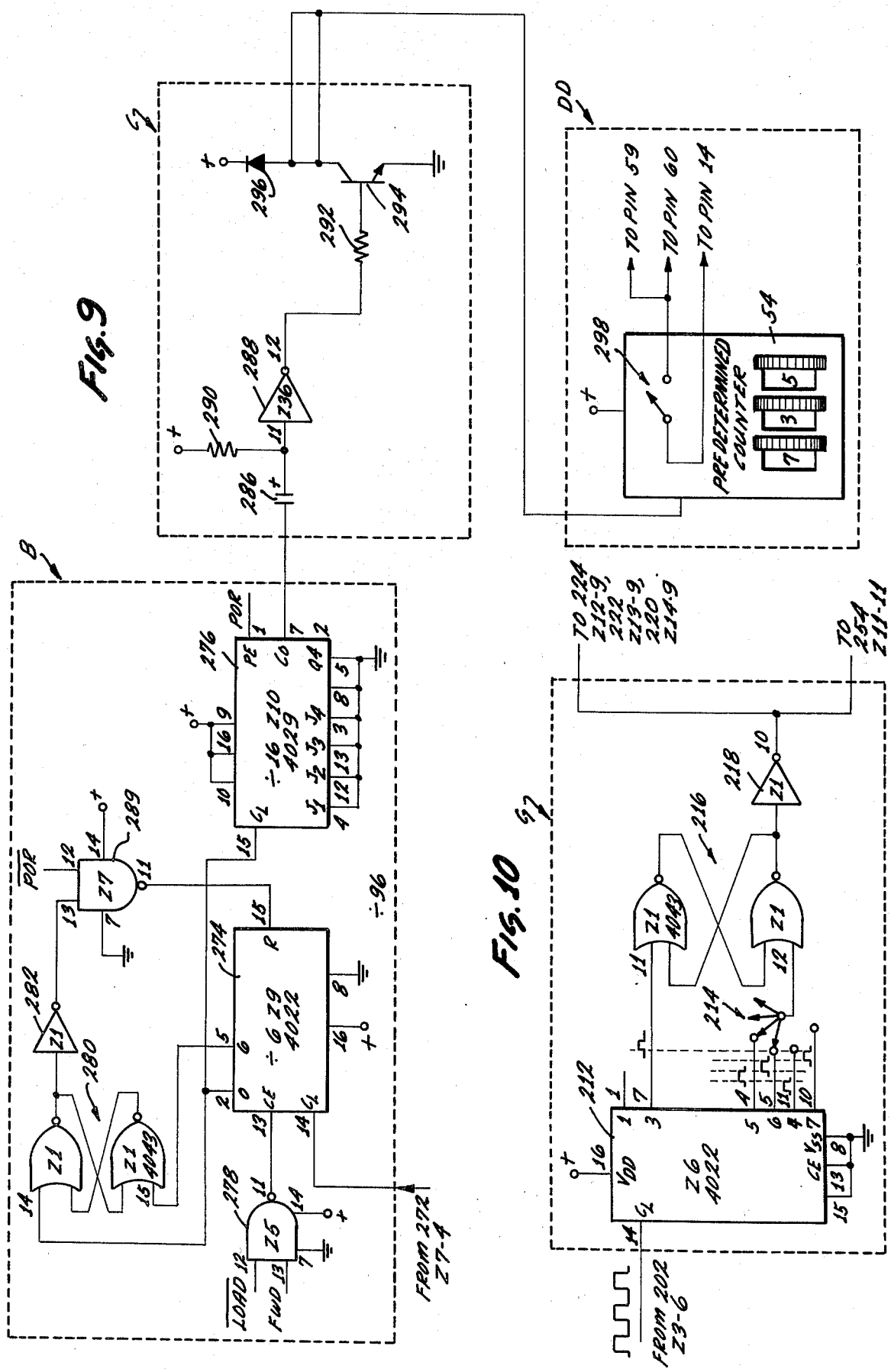

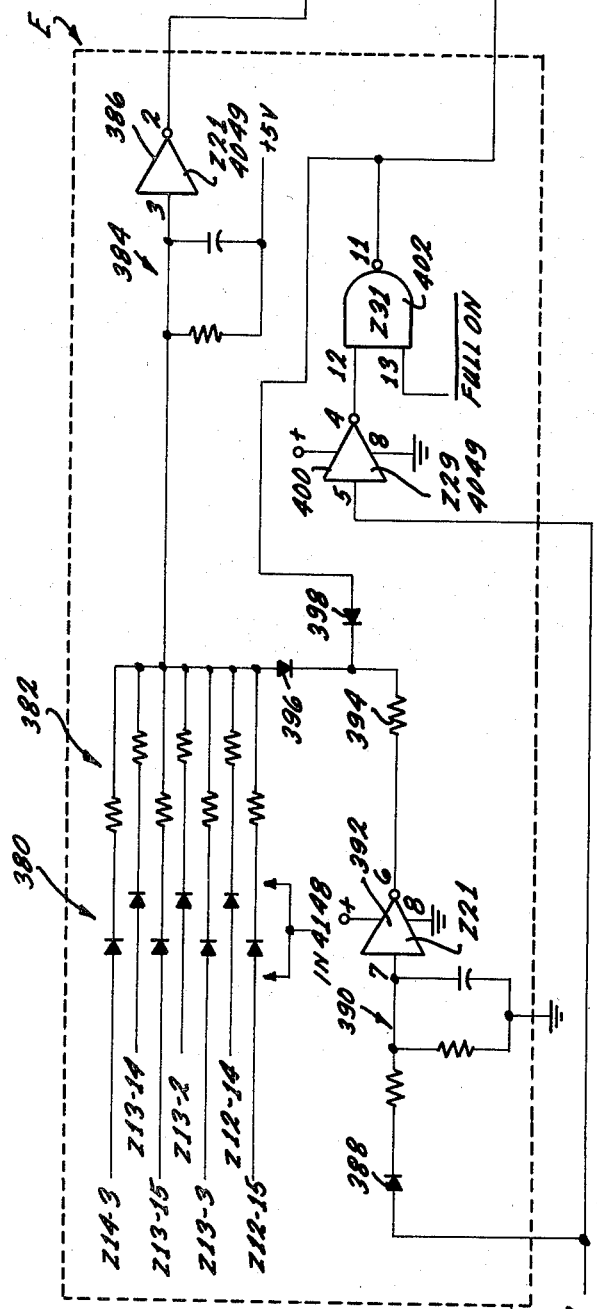
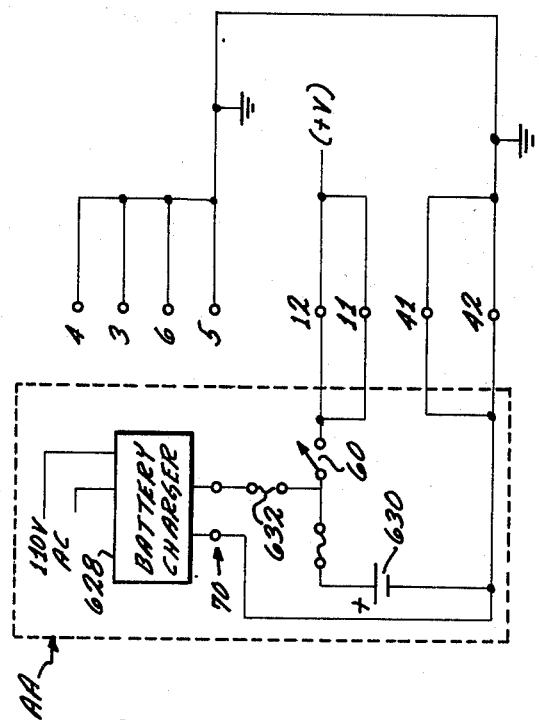

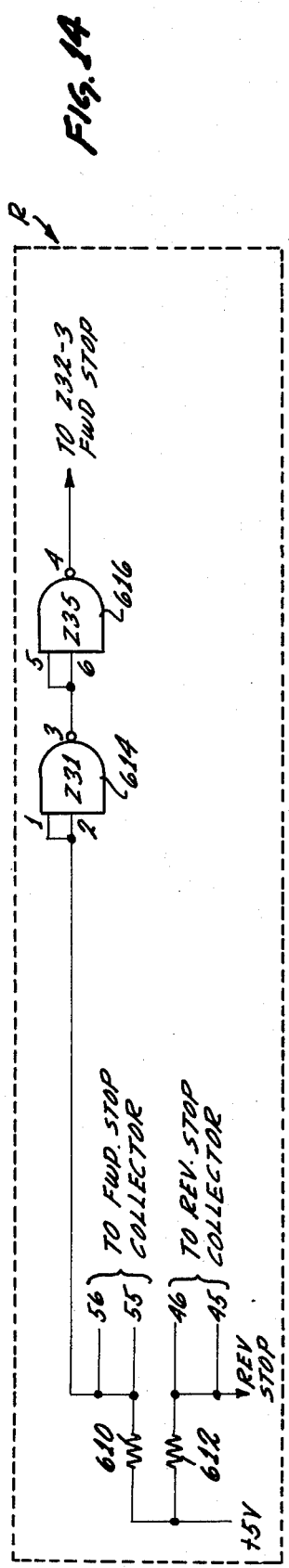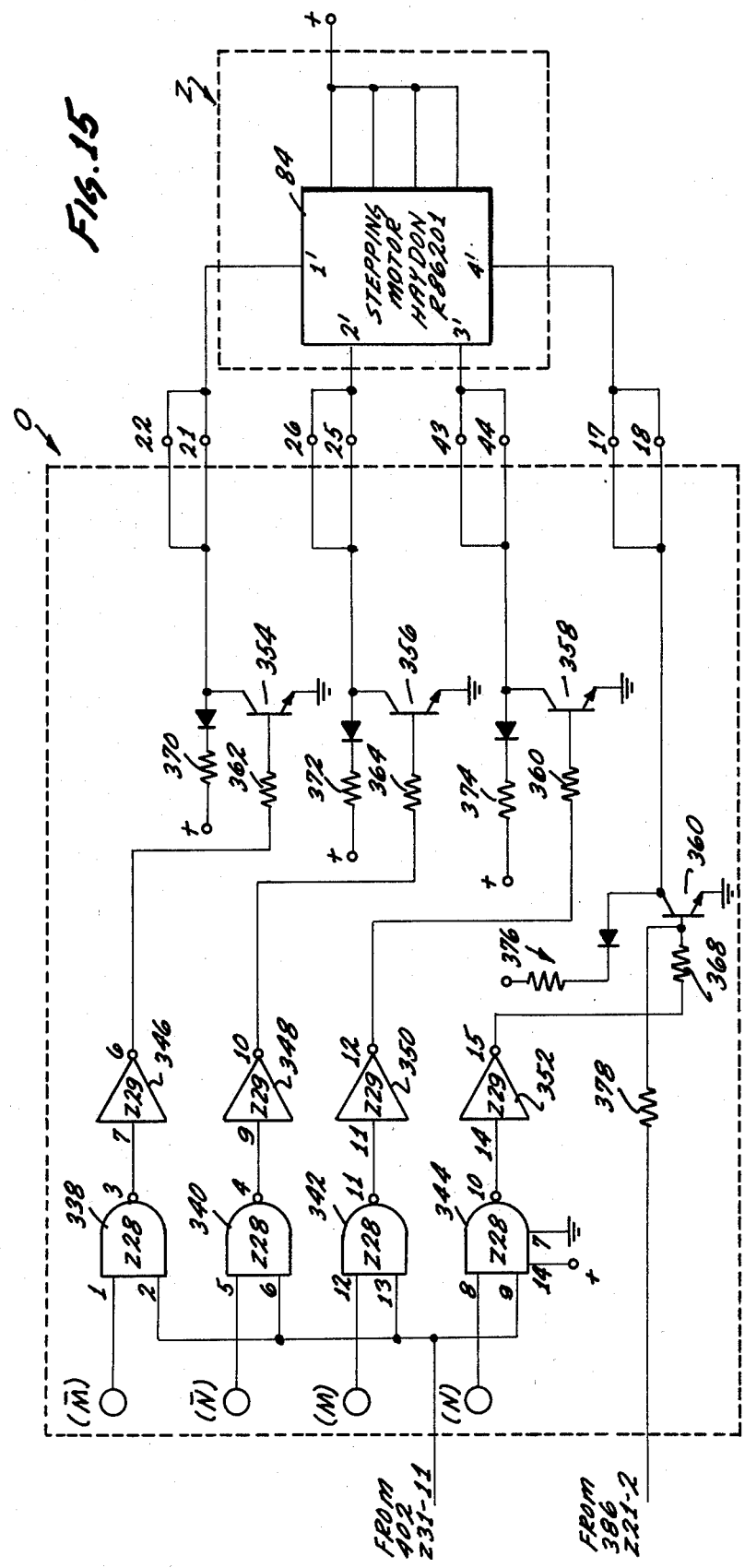
FIG. 14
FIG. 15

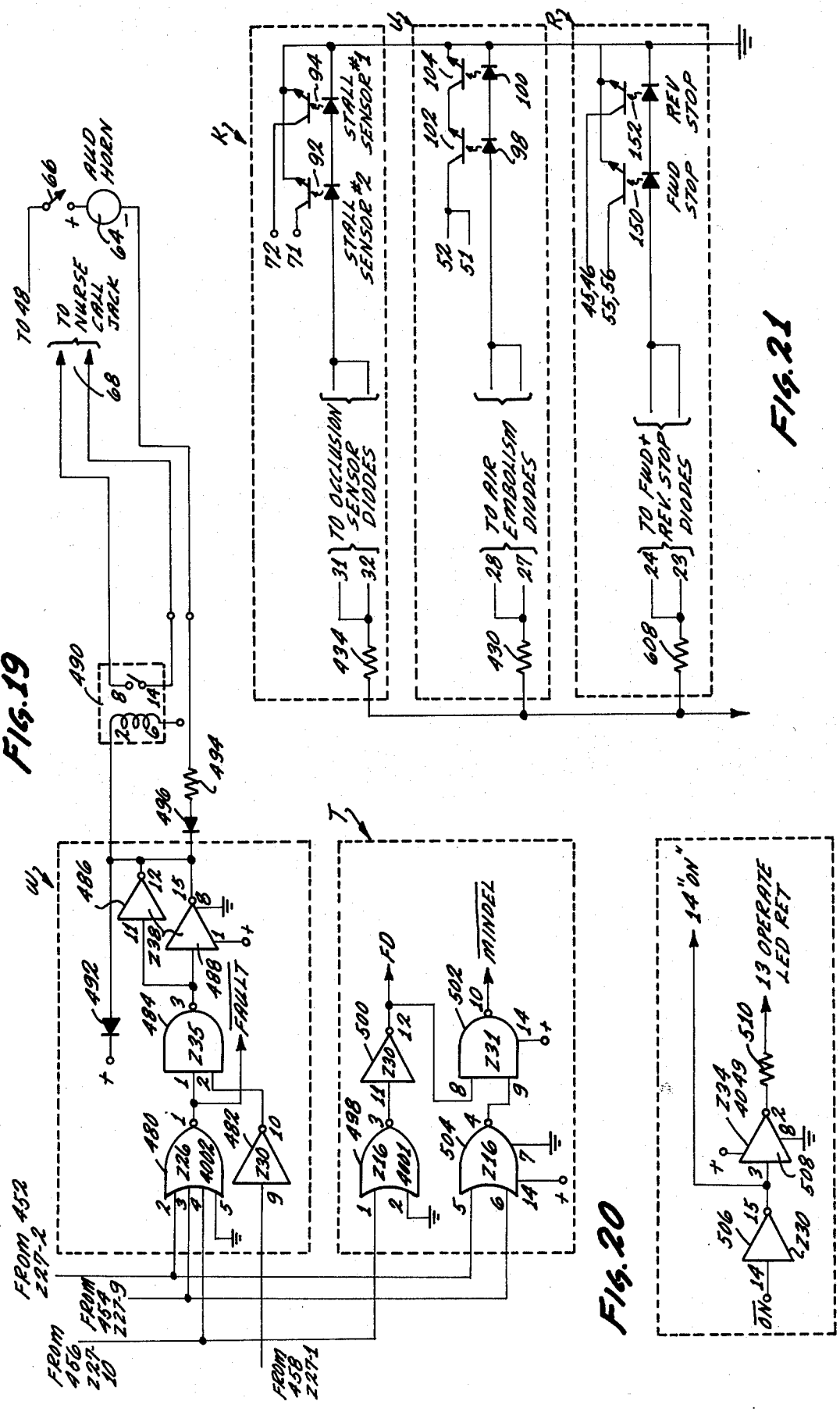

IV PUMP

The present invention is directed to a volumetric infusion pump for use in administering fluids intravenously to a patient. It is to be appreciated that the pump may be used for pumping fluids other than for intravenous administration of fluids but the invention will be described with reference to such intravenous administration of fluid to a patient.

It is desirable, when administering fluids intravenously to a patient, that the rate at which the fluid is administered and the total quantity of such administered fluid be accurately controlled. The most common method of of administering such fluids is through the use of a standard IV administration set and where a bottle of fluid to be administered is suspended in an elevated position and with the administration of the fluid to the patient passively provided by the operation of gravity.

The fluid from the elevated bottle may pass through a drip chamber and with the number of drops per minute being a coarse control of the rate at which the fluid is administered. The nurse must physically check the drip rate and the amount of fluid left in the bottle on a frequent basis, so as to manually adjust the drip rate when necessary, and to stop the administration of fluid when the proper quantity of fluid has been administered to the patient. The frequent checking by the nurse is time consuming, and the manual control of the rate of administering the fluid using the drip chamber is not very accurate.

In order to overcome the numerous problems of the administration of IV fluids using a nurse adjusted drip chamber, numerous pumps have been proposed to control the administration of the fluid to the patient. One such type of pump uses electronic means to detect the drip rate in a drip chamber and to automatically control the drip rate in a drip chamber and to automatically control the drip rate in accordance with the detected rate. This type of pump may also include a cam-like member to massage the IV tube to provide a positive pumping action to the fluid being administered to the patient. Although this type of pump is an improvement over using the elevated bottle and IV administration set with gravity, it still has some limitations as to the accuracy in the rate of pumping and in the pumping of a controlled volume of fluid to the patient.

Another type of pump which has been proposed, is to eliminate the elevated bottle of fluid and to use a large volumetric chamber which is filled with the fluid to be pumped. The entire chamber is then slowly emptied, using any one of a number of ways, and with the rate of emptying controlled to provide the control of the administration of the IV fluid to the patient. This type of pump has several disadvantages including the fact that the standard IV bottle and administration set is not used and a special, costly, chamber must be filled with the fluid to be infused. If this chamber is disposable, the cost of providing such a special large chamber filled with the desired fluid is relatively high compared with standard IV bottles and sets and if the chamber is not disposable, then the chamber must be cleaned and sterilized after each use. In addition, if the rate of infusion is to be low, it might be difficult to accurately control such a low rate of infusion from a large volumetric chamber.

The present invention overcomes many of the difficulties of the prior art methods of administering IV fluids and specifically, provides for the positive pumping of an IV fluid to a patient at an accurately controlled predetermined rate until a predetermined quantity of fluid has been administered and with a number of safety devices to insure that the pumping is either stopped or reduced to a very low rate when certain predetermined conditions occur.

For example, if air is detected in the line, then the pump is deactivated and cannot be restarted until the air-in-line condition is cleared. If the charge on the battery is low, an alarm is given even though the pump will continue to operate. When the charge on the battery drops below a level sufficient to drive the pump, then the pump is deactivated until the battery is either recharged or replaced or until the battery charger is connected to the battery to both recharge the battery and supply power to drive the pump. When the IV tubing is occluded beyond the pump's capability to pump, then the occlusion alarm is activated and the pump is deactivated until the alarm condition is cleared. Finally, when the predetermined volume of fluid has been infused into the patient, then the infusion complete alarm is activated and the pumping rate is reduced to a very low flow rate until the nurse either turns off the pump and removes the IV administration set or attaches a fresh supply of fluid and presets the pump to pump an additional amount of fluid to the patient.

The volumetric infusion pump of the present invention provides for the controlled pumping of a fluid through the use of a standard IV administration set which feeds fluid into a disposable volumetric cassette from an elevated bottle of fluid. Specifically, the cassette is of a syringe type, having a chamber of a predetermined volume and a plunger piston which is used to empty the chamber when connected to and driven by the pump. The pump includes a driver shuttle which is coupled to the bottom of the plunger to control the pumping of the fluid out of the cassette at a predetermined rate. Specifically, a stepping motor is used to drive the plunger at a controlled rate in accordance with the number and rate of pulses provided to the motor.

The volume of the chamber in the cassette is relatively small when compared with the volume of fluid which is normally to be pumped for infusion into the patient. For example, the volume of the cassette may be 5cc and generally, the volume of a fluid to be infused into a patient is a large multiple of 5cc. For example, the patient may receive 500, or 1000cc of a fluid so that the cassette must be filled and at least partially emptied a predetermined amount a large number of times in order to pump the fluid for infusion into the patient. Since the cassette is small in size it may be relatively inexpensive so that a new sterilized cassette can be used for each infusion of fluid, and with the cassette being discarded after the infusion is complete. The pump itself is designed to never contact the fluid as it is infused into the patient, so that the pump does not have to be sterilized after each use. Therefore, the only part of the combination of the pump and cassette which is in contact with the fluid is the inexpensive disposable cassette.

Generally, the casette is supported by positioning means on the pump so that the driver shuttle of the pump engages an extension of the cassette plunger and the tubing from the fluid bottle is connected to the input of the disposable volumetric cassette. The output tubing from the disposable cassette passes through an air-in-line sensor and is then coupled for infusion into the patient. The pump includes presetable dials which are adjusted to the volume of fluid to be infused and to the rate at which such volume is infused. After the air in the lines to and from the cassette are purged, so that there is only fluid in the lines from the fluid bottle to the patient, then the pump is operated to drive the plunger of the cassette to infuse fluid at the preset rate of infusion and until the preset volume of fluid is infused.

The cassette is at least partially emptied a predetermined amount and refilled many times during the infusion of fluid and the plunger, during refills, is rapidly operated in the direction opposite to the pumping direction. The portion of time used to refill the cassette chamber is relatively small in comparison with the time during which the chamber is emptied, but in order to insure that the pumping of the fluid for infusion occurs at an accurate rate, the time that it takes to refill the cassette chamber is detected and the stepping motor driving the plunger is fed additional pulses in the next delivery stroke to compensate for the time lost in refilling the cassette chamber.

It can be seen, therefore, that the volumetric infusion pump of the present invention operates using an inexpensive, sterilized, disposable cassette which is discarded after each use, and with the cassette including a volume chamber having an accurate cross sectional area which is filled and at least partially emptied a plurality of times before the predetermined quantity of fluid is infused into the patient. The rate of the fluid being infused is accurately controlled by using a stepping motor to drive the plunger within the cassette chamber and any time lost in refilling the cassette is compensated by feeding additional compensating pulses to the stepping motor. The accuracy of the cross sectional area of the chamber controls the accuracy of delivery of fluid and any inaccuracies in the volume of the chamber do not enter into the rate of infusion.

The volumetric infusion pump of the present invention includes numerous safety features as generally outlined above. It is important that the pump operate accurately as to the volume of fluid pumped and the rate of pumping, but is is also important that the pump does not endanger the health of the patient by attempting to pump fluid unless the flow of fluid to the patient is uninterrupted. For example, the volumetric infusion pump of the present invention includes an air-in-line detector which detects any air in the line to the patient. When such air in the line is detected, the pump is immediately stopped so as to insure that air is not infused into the patient. For example, should the bottle run dry, then ultimately air is present in the fluid line and moving towards the patient. At that time, the alarm is actuated and the pump is shut off to prevent any air being infused into the patient. Other conditions in addition to an empty bottle may cause air in the line, or the IV line may not be properly positioned in the air detector. In all of these conditions, the pump is stopped and the condition must be cleared before the pump can be restarted.

The pump also includes a battery alarm which provides an alarm signal when there is approximately one hour running time for the pump from the charge remaining on the battery. When the alarm initially comes on, the operation of the pump is not affected. If, however, the pump is operated beyond the alarm period without plugging in the battery charger, ultimately the battery is discharged so that there is insufficient power to drive the pump and this activates an occlusion alarm in addition to the battery alarm. The battery alarm can be cleared by connecting the battery charger to the battery, and after a brief period of time the pump may be operated through the battery charger while at the same time charging the battery.

The pump also includes an occlusion alarm to indicate to the operator that the IV tubing has been occluded beyond the pump's preset capability to pump, or when the battery power is insufficient to drive the pump. One major cause of this alarm condition is the tubing being occluded by the patient lying on the tubing. In addition, the tubing could be pinched such as in a bedrail, the filter could become clogged, or the tubing clamp from the bottle may not be open. In order to cancel the occlusion alarm, the cause of the occlusion must be eliminated before the pump can be reset to operate.

The infusion pump of the present invention also includes an infusion complete alarm, which alarm is designed to allow the operator to preset the volume that is to be infused into the patient, and to provide an alarm signal when that volume has been delivered to the patient. Specifically, the volume that is to be infused is set at the front of the pump using a counter dial. The pump automatically counts off the volume dispensed in 1 cc increments and displays the remaining volume to be infused on the volume dial of the pump. When the pump dispenses all of the desired preset volume of fluid, the dial shows zero and the infusion complete alarm is actuated. When the infusion complete alarm is actuated, the instrument is not shut off, but the flow rate from the pump is reduced to a very low keep-open rate of 1cc per hour. At this very low flow rate, the venipuncture cannula is less prone to being clogged before the operator can attend to the infusion complete alarm. In order to clear this alarm the pump is either deactivated or a new volume of fluid must be set into the volume-to-be-infused-dial, and if necessary, another source of fluid must be provided.

It can be seen, therefore, that the present invention provides for a very accurate volumetric infusion pump so as to control a volume of fluid to be infused into a patient at an accurately controlled rate using a standard IV administration set and fluid bottle. The pump includes a disposable volumetric cassette of small volume which is discarded after each use. A clearer understanding of the invention will be had with reference to the following description and drawings wherein:

FIG. 2 illustrates an exploded view of the portion of the pump for receiving the cassette and including a driver shuttle for connection to the cassette plunger;

FIG. 5 is a first view of an air-in-line detector for detecting air in the fluid line;

FIG. 6 is a second view of the air-in-line detector;

FIG. 7 is a functional diagram of the electronic control portion of the volumetric infusion pump of the present invention, and FIGS. 8 through 24 illustrate in detail a schematic diagram of the electronic control portion of the volumetric infusion pump of the present invention and specifically disclose the details of the functional blocks of FIG. 7.

Figure 1:
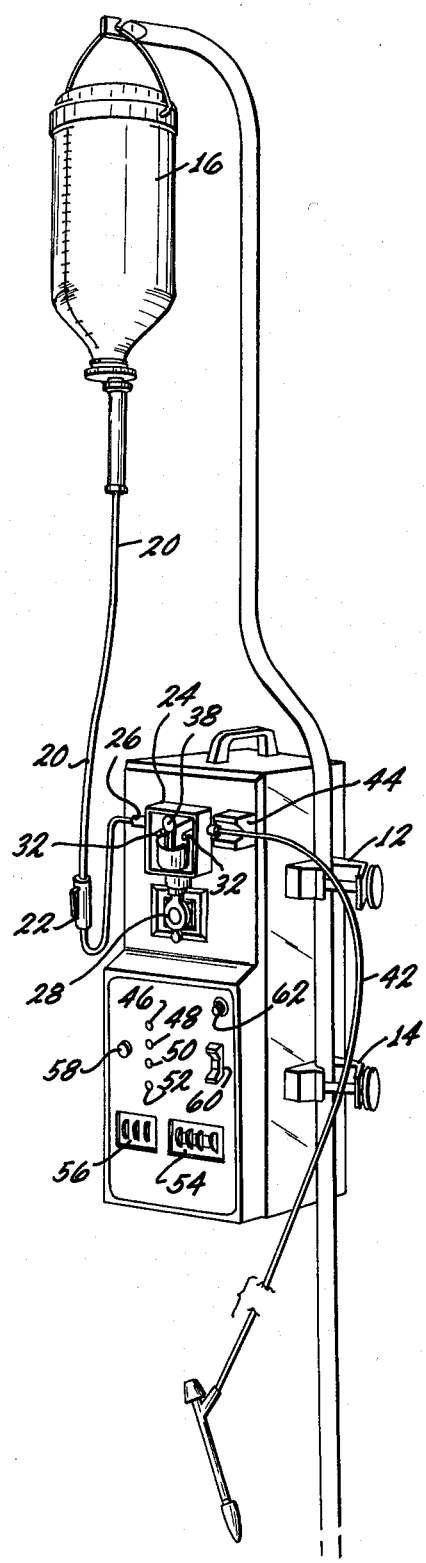
FIG. 1 illustrates a front isometric view of the volumetric infusion pump of the present invention.

In FIG. 1, an isometric view of a pump of the present invention is shown attached to a pole 10 using a pair of clamps 12 and 14. A standard IV administration set including a bottle 16 is also attached to the pole. The bottle 16 dispenses fluid to the pump through tubing 20 and it is to be appreciated that the pump will draw fluid by suction and the fluid bottle 16 need not be located above the pump. A clamp member 22 controls the flow of fluid from the bottle 16 for application to the pump.

The volumetric infusion pump of the present invention incorporates a disposable volumetric cassette 24 to receive fluid from the tubing 20 by connecting the tubing 20 to an input plug 26 of the cassette 24. The volumetric cassette 24 includes a plunger shaft 28 which includes an end portion which fits on a plunger shuttle 30. The plunger shuttle 30 extends from the pump and is used to drive the plunger shaft 28 in a vertical direction to control the flow of fluid into and out of the cassette. A pair of location pins 32 also extend from the pump and the cassette 24 includes openings 34 which snap over the pins 32. A valve motor shaft 36 also extends from the pump into a valve portion 38 of the cassette to control the valving of the fluid into and out of the cassette so as to provide for the alternate filling and at least partial emptying of the cassette during infusion of the fluid into the patient.

The output from the cassette 24 is taken from an output plug 40 and is then coupled through an extension tubing 42 and on to the patient for infusion into the patient. The extension tubing 42 is also positioned in an air-in-line detector 44 for detection of any air in the like to the patient. The details of the air-in-line detector 44 and the cassette 24 in combination with the control mechanisms of the pump will be explained in greater detail in later portions of this specification.

The volumetric infusion pump of the present invention includes a plurality of operating mechanisms and alarm indicators on the front panel and the back panel of the pump. For example, as shown in FIG. 1, a plurality of output indicators 46 through 52 provide alarm indications for particular alarm conditions. Specifically, alarm indicator 46 is an air-in-line alarm indicator. Alarm indicator 48 is a battery alarm indicator. Alarm indicator 50 is an occlusion alarm indicator, and alarm indicator 52 is an infusion complete alarm indicator. The control of the volume of liquid to be infused and the rate at which this liquid is to be infused is preset using dial mechanisms 54 and 56. Specifically, dial mechanism 54 is a volume-to-be-infused dial and includes output indicators which are counted down as the volume is infused. The dial 56 is a rate dial which can be preset to the desired infusion rate for the infusion of the liquid into the patient.

A push button 58 is a purge switch to initially purge the air in the line before infusion of the liquid into the patient. A switch 60 is an on-off switch and a push button 62 is an operate button to control the operation of the pump after the on-off switch has been switched to the on position.

Figure 4:
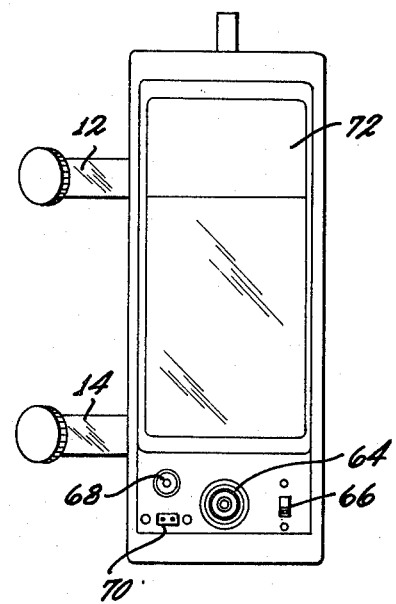
FIG. 4 illustrates a rear view of the pump of the present invention.

As shown in FIG. 4, the back panel of the volumetric infusion pump includes an audio alarm 64 and a switch 66 to control the audio alarm to be on or off. A receptacle 68 is used to provide an output signal at a remote location to indicate to the nurse or other personnel at such remote location that any of the alarm conditions have occurred at the pump.

A battery receptacle 70 is used for recharging the battery used to power the pump and a cover 72 is used to cover, but provide access to, the storage portion of the pump which contains the battery charger.

Figure 3:
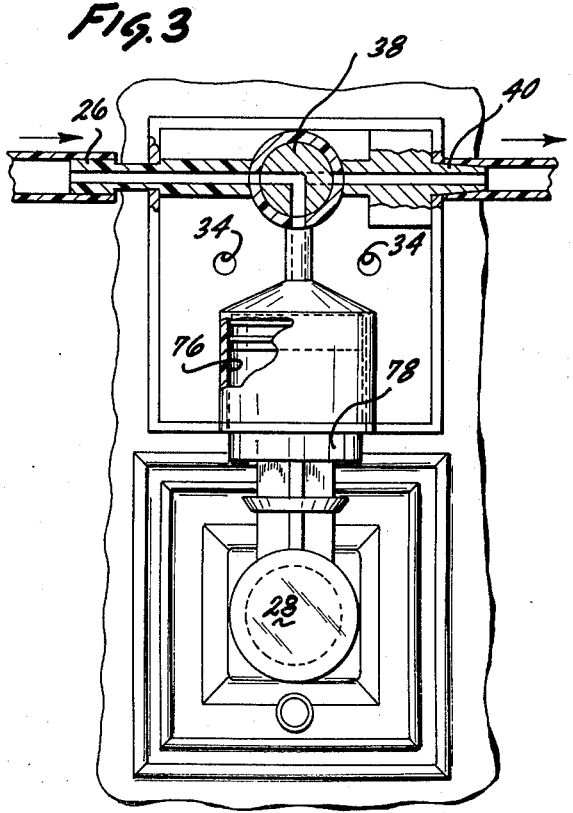
FIG. 3 illustrates in more detail a disposable volumetric cassette for use with the pump of the present invention.

FIGS. 2 and 3 show in greater detail the construction of the portion of the pump in combination with the cassette 24 which provides for the movement of the plunger shaft 28 of the cassette and the operation of the valve mechanism 38 of the cassette so as to control the flow of fluid through the cassette 24 from the input plug 26 to the output plug 40. As indicated above, the openings 34 in the cassette 24 snap over the pins 32 in the pump to lock the cassette in position. The valve motor shaft 36 is seated within the valve structure 38 of the cassette to control the position of the valve in accordance with the operation of a motor 74.

The valve 38 is a two-way valve type to allow for the passage of fluid from the input plug 26 to a volumetric chamber 76 for filling of the chamber for a first position of the valve 38. A second position of the valve 38 provides for the pumping of the fluid from the chamber 76 to the patient through the output plug 40. It can be seen, therefore, that by the alternate control by the motor 74 to control the position of the shaft 36, the valve mechanism 38 is controlled to allow for the alternate filling of the cassette chamber 76 and pumping of the fluid in the chamber to the patient. The actual filling and emptying of the fluid in the chamber 76 is in accordance with the movement of a plunger 78 within the chamber 76. The plunger shaft 28 is at the end of the plunger 78 and is connected to the plunger shuttle 30. The member 28 snaps over the plunger shuttle 30 when the cassette is snapped into position on the pump. The moving of the valve 38 between the two positions is coordinated with the moving of the plunger 78 in the two directions to provide for the filling and emptying of the chamber 76.

The plunger shuttle 30 is connected to a sliding structure 80 which is driven by a shaft member 82. The shaft member 82 is in turn rotated by a stepper motor 84. The shaft member 82 drives the slider member 80 through a lead screw and lead nut 86 to provide precise movement of the plunger shuttle 30. A disc member 88 containing a plurality of slots 90 is also coupled to the shaft 82 and two detectors 92 and 94 each formed by a light source and a light detector provide for detection of the rotation of the shaft 82 each time a slot passes by one of the detectors 92 and 94. The slotted disc member 88 and the detectors 92 and 94 are used to detect for an occlusion in the line by detecting stalling of the motor 84.

It can be seen with reference to FIGS. 2 and 3 that as the motor 84 is driven by stepping pulses, the shaft 82 rotates to provide vertical movement of the slider 80 and the plunger shuttle 30. This in turn provides vertical movement of the plunger 78 in the volumetric chamber 76 to either pump fluid in the chamber 76 for one position of the valve 38 and with the plunger 78 being moved in a controlled slow speed in an upward direction, or to draw fluid into the chamber 76 for a second position of the valve 38 and with the plunger 78 being momved at a rapid speed in a downward direction. The alternate rapid filling and slow pumping of fluid in the chamber 76 by the movement of the plunger 78 provides for an accurate control of the rate of infusion of fluid into the patient until a predetermined quantity of fluid has been infused.

FIGS. 5 and 6 illustrate in detail the air-in-line detector 44 shown in FIG. 1. As can be seen in FIGS. 5 and 6, the air-in-line detector includes a passage 96 which receives the tubing 42 shown in FIG. 1. A pair of light sources 98 and 100 are positioned above the passage 95 to provide light energy through the tubing 42 and specifically with each light source providing a beam of lilght from the outside of the tubing 42 through a point tangential to the inner bore of the tubing. The light source 96 provides detection of air in the line in the rearward half of the tubing 42 and the light source 100 provides detection of air in the forward half of the tubing 42. A pair of detectors 102 and 104 are positioned to detect the presence or absence of light refracted through the tubing-fluid composite. Since the composite refractive index of tubing containing fluid is relatively constant but significantly different from that of tubing with air the detectors 102 and 104 provide output signals which differentiate between the two conditions.

The volumetric infusion pump of the present invention is generally operated by a nurse or other hospital personnel in the following manner. The rate dial 56 is initially set to zero before the on-off switch 60 is moved to the "on" position. The air-in-line alarm indicator 46 is now activated and stays lit until the tubing 42 is placed in the air detector 44 and until the air in the tubing 42 has been purged from the system. The purge switch 58 is pushed in and maintained in that position until the slot at the end of the valve motor shaft 36 is at a 45° angle to the left. This is the position of the valve motor shaft 36 shown in FIG. 2.

The volumetric cassette 24 is now snapped into position over the cassette locator pins 32 and with the valve 38 locked into the slot at the end of the valve motor shaft 36. The cassette plunger shaft 28 is then positioned over the plunger shuttle 30 and pressed to snap into a locked position. The extension tubing 42 is now positioned into the air detector 44 and coupled to the output plug 40 of the cassette.

The IV administration set including the tubing 20 is now filled from the fluid bottle 16 before the tubing 20 is connected to the input plug 26 of the cassette. The clamp 22 is maintained in the open position and the purge switch 58 is pushed to operate the pump in the purge mode until the cassette 24 and the extension tubing 42 all the way down to the venipuncture cannula at the end of the extension tubing 42 are void of air. At this time, a puncture may be made into the patient's vein for the infusion into the patient of the fluid from the fluid bottle 16 and under control of the pump of the present invention.

The rate dial 56 is now set to the desired rate in cc per hour. The volume-to-be-infused dial 54 is then set to the desired volume of fluid to be infused into the patient. The operate button 62 is then pressed to begin the infusion of the fluid into the patient.

During the operation of the volumetric infusion pump of the present invention, a number of alarm conditions may occur, and the pump is designed to provide safety for the patient by controlling the operation of the pump in accordance with the alarm condition. In order to insure a rapid clearing of the alarm condition, the alarms provide a visual diagnosis of the reason that the instrument has been alarmed. A particular one of the indicators lights when a specific alarm condition occurs but any of the alarm conditions provides an audible alarm from speaker 64 when so controlled by the audible alarm on-off switch 66.

The specific alarm conditions are air-in-line, low battery, occlusion, and infusion complete. The air-in-line alarm is activated when the bottle 16 runs dry or any other condition which would cause any air on the output side of the cassette which would be moving towards the patient, or if the IV tubing 42 is not placed in the air detector 44. When this alarm condition occurs, the pump shuts off and the output light 46 is activated. The pump cannot be restarted until the air-in-line condition is cleared. Once the air-in-line condition is cleared. Once the air-in-line condition is cleared, the pump may be restarted by pressing the operate button 62.

The battery alarm is activated when there is approximately one hour running time remaining on the battery charge. The alarm provides an ouput indication by the output indicator 48, but the pump continues to operate. If, however, the pump is operated for more than one hour without plugging in the battery charger to recharge the battery, the battery discharges and there is insufficient power to drive the pump which in turn activates the occlusion alarm. The battery alarm condition can be corrected by plugging in the battery charger to the battery and allowing the battery to charge for a short period of time, such as two or three minutes, and then pressing the operate button 62. The pump is now operated through the battery charger while charging the battery.

The occlusion alarm is activated when the IV tubing has been occluded beyond the instrument's preset capability to pump, or when the battery is discharged, so that there is not sufficient power to drive the pump. Other causes for activating the occlusion alarm may be that the tubing is occluded by the patient lying on the tubing, the tubing may be pinched in a bedrail, or the tubing may be pinched by some other physical element. In addition, the filter in the IV set may be clogged, or the tubing clamp 22 from the bottle 16 may be closed. In order to cancel the occlusion alarm, the particular cause of the occlusion must be eliminated and then the operate button 62 must be pushed.

The infusion complete alarm is activated once the predetermined volume has been infused into the patient. This alarm allows the operator to preset the volume of fluid that is to be infused and when that volume of fluid has been delivered, the infusion complete alarm is activated. The volume-to-be-infused dial 54 is set to the desired volume to be administered and as the volume of fluid is being infused into the patient, the pump automatically counts off the volume dispensed to the patient, and displays the remaining volume to be infused on the dial 54. When the dial 54 reaches zero, the instrument displays an alarm condition by activating the indicator 52, and then shuts down the flow rate of the infused fluid to a very low keep-open rate of 1cc per hour. This keep-open flow of fluid prevents the venipuncture cannula from being clogged until the operator can attend to the pump. To clear the infusion complete alarm, a new volume of fluid must be set into the volume-to-be-infused dial 54 and if necessary, another source of fluid such as a new bottle 16 must be provided.

The control of the operation of the pump to administer fluid to a patient in accordance with the preset conditions is controlled by the electronics portion of the pump which is mounted in a conventional way on a printed circuit board and is contained within the casing of the pump. A functional diagram of the electronic portion of the pump is shown in FIG. 7 as a series of blocks labeled, in alphabetical order, A through Z and AA through DD. In FIG. 8 through 24, the details of the circuitry necessary to provide the particular functions are shown and the dotted blocks, also labeled A through Z and AA through DD, correspond to the blocks as shown in FIG. 7. Keeping in mind the specific details of the circuits shown in FIGS. 8 through 24, a general description of the functional operation of each block shown in FIG. 7 will be given.

Block A is indicated to be the slew control. It is the function of block A to receive the commands to determine the direction of rotation of the stepper motor 84 which drives the shuttle 30, which in turn, drives the plunger 78 in the cassette 24. Block A also contains the purge control switch functions.

Block B provides a divide-by-96 function and is so labeled. The circuitry of block B is used to count the motor drive pulses and when 96 pulses have been accumulated, a pulse signal is provided from block B which pulse signal is coupled to block C. The function of block C is to provide a driver pulse for a predetermined counter whic counter includes the volume-to-be-infused dial 54, shown in FIG. 1. Block DD represents the predetermined counter itself and is so labeled. As indicated above, the predetermined counter includes a volume-to-be-infused dial 54 which is used to set the volume of fluid which is to be infused into the patient.

In the pump of the present invention, 96 motor pulses are the equivalent of 1cc of fluid being administered to a patient so that each time 96 pulses are counted by block B, the driver C counts the predetermined counter DD down by one. The dial 54 also includes output indicators which are counted down to zero as the pump operates to administer fluid to a patient to provide a visual indication at all times of the volume of fluid still remaining to be infused into the patient. When the predetermined counter DD counts down to zero, the normal operation of the pump is stopped and the pump is shifted into a keep-open mode, as described above, where the pump operates to administer fluid at a very low rate. The block DD includes a contact closure which is used to indicate that an infusion is complete.

The function of block K is to provide a motor stall detector circuit and the block K receives pulses from two stall sensors which determine when the motor 84 shown in FIG. 2 is stalled. Specifically, the pulses received from the stall sensors are used to reset a counter located within block K.

The stepping motor driver circuit represented by block O drives the stepping motor represented by block Z in accordance with stepping pulses. These stepping pulses are also accumulated in the motor stall detector circuit K as the stepping motor 84 advances. As shown in FIG. 2 the small disc 88 on the shaft of the stepping motor 84 is used to provide stall sensor pulses which pulses reset a counter within the stall detector circuit K to zero each time a slot 90 passes by one of the photodetectors. If the motor stall detector circuit K receives more motor drive stepping pulses than can be accumulated within the counter before receiving a stall sensor reset pulse, this provides an output signal from the block K. This output signal indicates that although motor stepping pulses are being supplied to the motor 84, the shaft 82 is not moving and the pump must be stalled.

The block L represents the stepper motor drive logic circuit which circuit provides output signals representing whether the motor is to be driven clockwise or counterclockwise. These signals are alternately provided to the stepper motor driver circuit O.

Block P represents the latches for the fault and sensor output circuit and block P is used to individually activate the indicators such as LED indicators shown on the face of the pump in FIG. 1. Specifically, the LED indicators are designated as indicators 46 through 52 and these indicators provide a visual alarm of a problem in the operation of the pump. The indicators 46 through 52 designated as block X are driven by the LED drivers represented by block T. The output signals from Block P, representing the various alarm conditions, are also supplied to the fault and indicator controls represented by block T which controls the operation of the pump in accordance with an alarm condition. Block W represents the nurse call relay driver which provides the nurse call output signal at the nurse call receptacle 68 shown in FIG. 4.

Block D represents an oscillator and specifically a 211.11 hz oscillator. This oscillator provides pulses to a pulse width control circuit represented by block G. The output pulses from the block G in turn drive a three decade rate scaler represented by block I. The scalers in block I are controlled by digital switches represented by block BB, which digital switches are formed by the rate dial 56 shown in FIG. 1. The settings of the switches forming the rate dial 56 are used to provide motor drive stepping pulses at the right frequency so as to administer the fluid to the patient at the predetermined rate.

Block J represents a refill time rate compensation circuit which is used to accumulate pulses during the time that the cassette chamber 76 is being refilled by moving the plunger 78 in the reverse direction. As the plunger starts to move forward again to pump fluid, the block J provides for compensation for the lost time by adding to the motor drive pulses the additional pulses that were accumulated during the refill time so that the accuracy of the rate of administering the fluid is not impaired by the periodic stopping of the pumping to refill the cassette chamber.

Block M represents an audible and LED period timer and is used to provide for a beep rate for the audible alarm 64 shown in FIG. 4 and for a flashing of the indicators 46 through 52. A low battery detector circuit represented by block N initially turns on the alarm indicator 48 and for a predetermined period of time, such as an hour, the pump will operate even though indicator 48 represents a low battery. When the battery is discharged and thereby insufficient to drive the pump, then the instrument is turned off and the occulsion indicator 50 is activated in addition to the indicator 48. Block N therefore detects the condition when the battery is low, but still has sufficient power to run the pump and with a low battery alarm indication provided by the indicator 48 and with the pump continuing to operate to administer fluid to a patient. A second stage is reached where the charge on the battery is insufficient to drive the pump and at that time, the occulsion indicator 50 is additionally activated.

Block Q represents a power on reset circuit and when the power is first turned on, the output from the block Q provides that all the circuits are set to the proper condition. The block Q insures that the pump is not in an operate mode without first pressing the operate button, or that other undesirable operations do not occur unless properly activated.

Block R represents the forward reverse logic and the output from Block R is responsible for determining the direction of rotation of the DC motor 74 shown in FIG. 2 which motor is used to operate the valve 38 in the cassette. Block R receives inputs from the DC motor control logic and drive circuit represented by block S. Specifically, block S includes a pair of position sensors to detect the position of the slider mechanism 80 at the upper and lower positions. The detection of these positions indicates that a reversal of the direction of motor 84 is necessary and also that the motor 84 must be controlled to control the position of the valve in the cassette. The position sensors are shown in FIG. 2 and include two pairs of light emitters and detectors 150 and 152.

Block U represents the light emitter and detector combinations used for detecting the air-in-line, or an air embolism. The structure of these sensors are shown in FIGS. 5 and 6.

As indicated above, block T represents the fault and indicator controls and block T contains the coding networks to determine the actions that are taken during an alarm condition. Specifically, the pump is either maintained in a keep-open rate or is shut off entirely during an alarm condition. In addition during the initial low battery alarm condition the pump is maintained in an operating condition. The keep-open rate is maintained after the infusion complete but there is no keep-open rate when there is air in the line, an occulsion of the line, or when the battery is dead.

Block AA represents a battery charger and is used to charge the battery through the receptacle 70 shown in FIG. 4.

Turning now to FIGS. 8 through 24, which figures illustrate in detail circuits to form the blocks shown in FIG. 7 and also illustrates interconnecting portions between the blocks shown in FIG. 7. In FIGS. 8 through 24, the various portions of the circuit which correspond to the blocks shown in FIG. 7 are surrounded by dotted lines and the portions surrounded by lines are identified by the same alphabetical reference provided for the blocks shown in FIG. 7.

Figure 8:
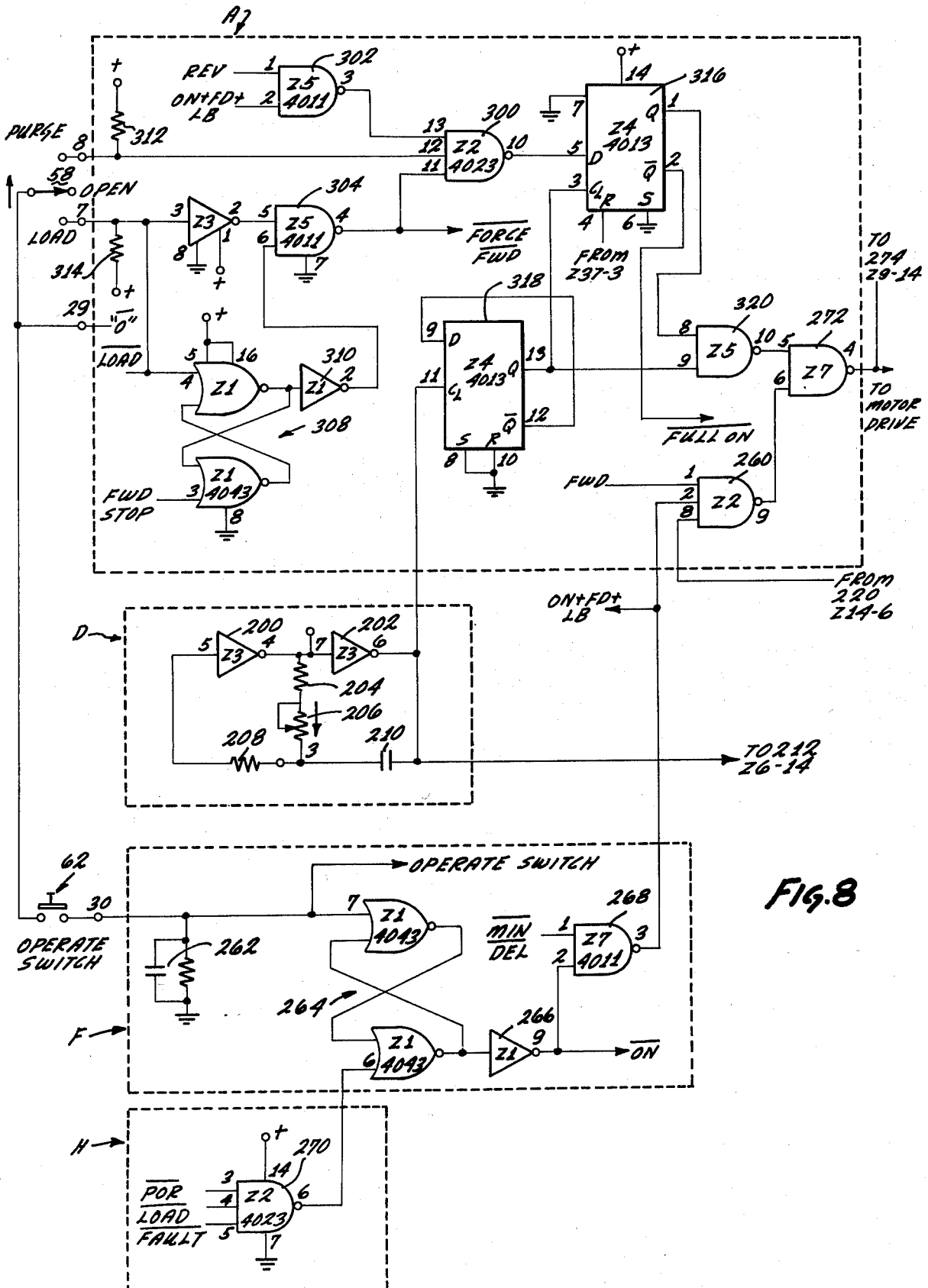

The oscillator block D is shown in FIG. 8 and includes a pair of inverters 200 and 202. A variable resistance network including resistor 204 and potentiometer 206 is coupled between a junction between the inverters and a junction between a resistor 208 and a capacitor 210. The pair of inverters 200 and 202 provide for the polarity of the voltage potential across the capacitor 210 to alternate so that the direction of charging the capacitor is alternated. For example, as the capacitor 210 is charging in one direction, the voltage at the input to inverter 200 has a positive or negative potential depending upon the direction of charging of the capacitor 210. This provides for a similar positive or negative potential at the output of inverter 202 so that the polarity at the other side of the capacitor 210 tends to reverse the direction of charging. It can be seen, therefore, that the charging of the capacitor alternates so as to provide for an oscillating voltage pulse output from the oscillator D. The oscillating voltage output from the oscillator is a basic reference signal used in the electronic portion of the pump and may have a frequency of 211.11 hz.

The pulse signal from the oscillator D may be used as an input to the pulse width control block G shown in FIG. 10. Specifically, the pulse signal may be applied to a counter divider 212. This counter divider may be a conventional four stage divide by eight Johnson counter. The counter is advanced by the positive pulse signal applied to the clock input. Four of the clock outputs are used with a switch 214 so as to provide for an output signal having a desired pulse position as shown by the position of the pulses next to the four output positions in accordance with the position of the switch 214. The output signal from the counter divider is applied to a latch circuit 216 as the set input and another one of the outputs from the counter divider 212 having a pulse position as shown is applied as the reset input to the latch circuit 216. The difference between the set and reset inputs to the latch 216 provide for variable pulse width signals from the latch 216 in accordance with the position of the switch 214. The counter divider 212 may be a monolithic silicon digital integrated circuit of a conventional type such as an RCA type CD 4022. The latch 216 may be one of a number of such latches contained on a monolithic silicon digital integrated circuit such as RCA type CD 4043.

The counter divider 212 therefore provides an output signal having a particular pulse position once in each cycle of eight input pulse signals and with the output signal used to set a latch circuit. The latch circuit is reset once each cycle so as to provide an output signal to an inverter 218 having a frequency equal to one eighth of the input signal to the pulse width control G. The pulse width of the output signal in accordance with a desired pulse width as chosen by the switch 214. Specifically, the particular pulse width is chosen on an individual basis so as to provide the appropriate pulse width to drive the stepping motor 84. This is necessary since some stepping motors require a greater pulse width signal than others to provide for the drive of the stepping motor.

Figure 16:
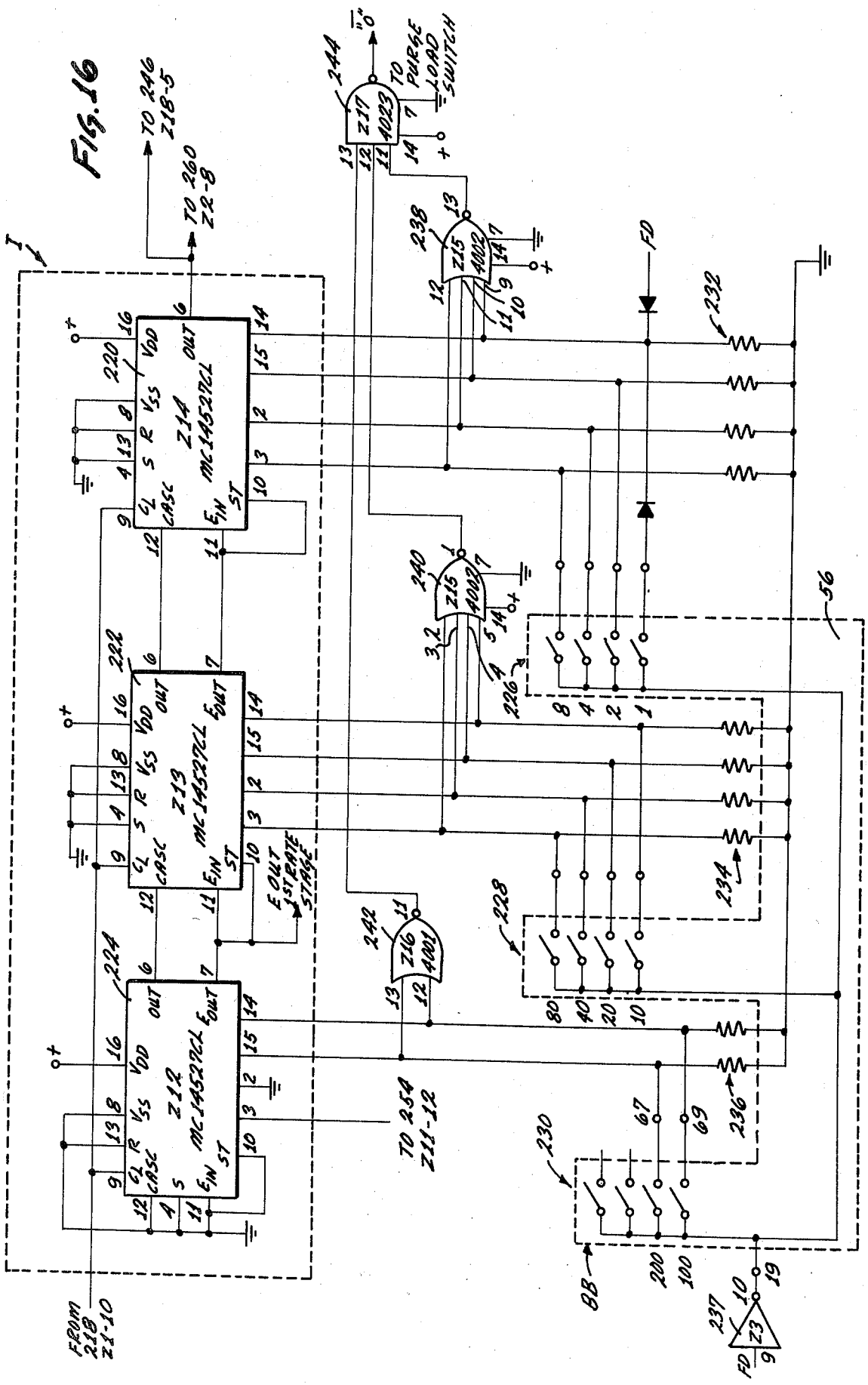

An output signal from the pulse width control block G is applied to the block I shown in FIG. 16 which block contains the decade rate scaler. The decade rate scaler includes three decade counters 220, 222 and 224 used for the ones, tens and hundreds of the rate control of the pumped fluid. The operator control of the rate is provided by the digital switch BB which is formed by the rate switches 56 on the front panel of the pumps. Specifically, the switches 56 include switches 226, 228, and 230 for the ones, tens, and hundreds and although the visual indications to the operator of the pump are decimal in character, the switches provide for BCD inputs to the decade rate scaler as shown in block I.

When the operator of the pump adjusts the switches 226, 228 and 230 to the desired rate at which the fluid is to be administered, the BCD inputs to the decade counters 220, 222, and 224 and the input line clocking signal control, the decade rate scaler to provides an output signal having a pulse rate per unit time in accordance with the setting of the switches 226, 228 and 230. A plurality of resistive groups 232, 234 and 236 are used to provide bias of the BCD input signals to the decade rate scaler as shown in block I. An input signal to the switches 226, 228 and 230 is provided through an inverter 237 and with the input to the inverter being a finish delivery signal. A plurality of NOR gates 238, 240 and 242 are used in conjunction with a NAND gate 244 to insure that a purge of the pump can only occur when all of the switches 226, 228 and 230 have been set to zero on the front panel dial 56.

Figure 17:
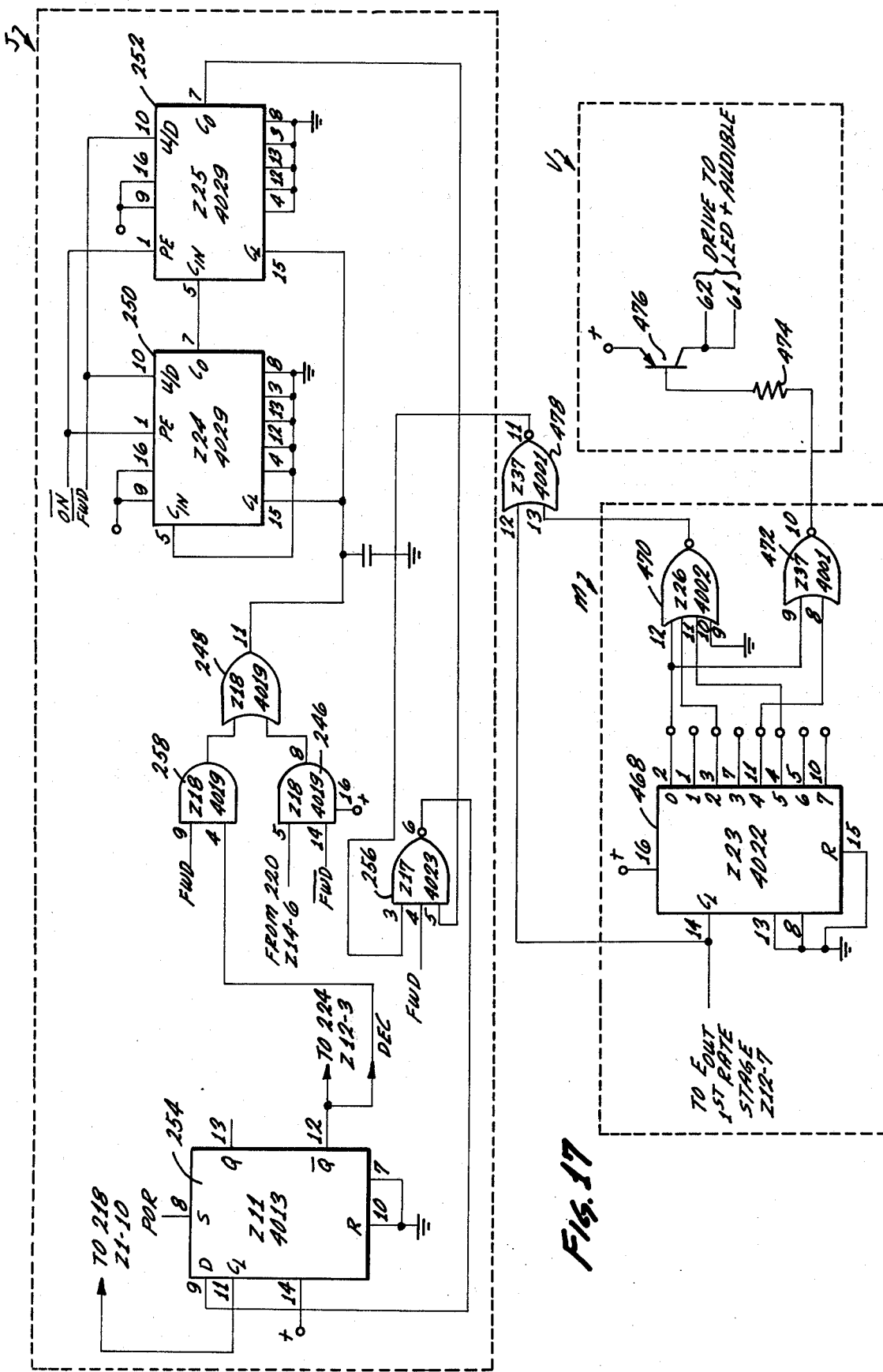

The output signal from the decade rate scaler as shown in block I are the motor drive pulses and these pulses are applied to the slew control block A shown in FIG. 8 and the reverse time rate compensation circuit block J shown in FIG. 17. Specifically, the motor drive pulses applied to the reverse time rate compensation circuit block J are applied as one input to an AND gate 246. The other input to the AND gate 246 is a not forward signal. Therefore, there is an output from the AND gate 246 when the pump is not forward in direction. The output from the AND gate 246 is applied as an input to an OR gate 248 and with the output from the OR gate 248 used as a clocking input to a pair of counters 250 and 252. The counters may be a four stage up-down counter including the clock input, a carry in input, jam inputs, an up-down input, and a preset enable input. The counters also include a carry out signal an an output. The up-down counter may be of a conventional type and may, for example, be a monolithic silicon digital integrated circuit and may be an RCA type CD 4029.

The counters 250 and 252 only accumulate pulses from the OR gate when a not-on signal from the pump used as a preset enable is low. The counter counts up when the up-down signal is high and counts down when the up-down signal is low. The up-down signal is provided by the not-forward signal and it can be seen that the not-forward signal is high to count up when the pump is refilling the cassette, and the not-forward signal is low to count down when the pump is emptying the cassette. Output pulses are therefore accumulated by the counters 250 and 252 as the pump is refilling the cassette and these pulses are then counted down when the pump is emptying the cassette.

The output signal from the counters is applied to a flip-flop 254 through a NAND gate 256. The NAND gate is used to insure that the counter output is applied to the flip-flop 254 only when the pump is in the forward direction, and when there is a signal from the period timer block M.

The flip-flop 254 is clocked by the output signal from the pulse width control block G so that the logic level opposite to that present at the "D" input is transferred to the Q output during the positive-going transition of the clock pulse from the pulse width control block G. The output from the flip-flop 254 is used as an input to counter 224 so as to periodically adjust the rate of output pulses to the stepping motor to a higher rate in accordance with the clocking of the flip-flop until all of the pulses have been counted down by the counters 250 and 252.

The output signal from the flip-flop 254 is also used as an input signal to an AND gate 258 which, in conjunction with the forward signal provides a second input signal to the OR gate 248. The output signal from the OR gate 248 is the clock input to the counters 250 and 252 and during the forward operation of the pump, this clock input provides for the countdown of the accumulated pulses.

The pulse rate signal to drive the stepping motor is applied as one input to a NAND gate 260 shown in FIG. 8. The second input to the NAND gate 260 is the forward signal and the third input to the NAND gate is from the start/operate latch circuit block F. When the operate switch 62 is activated in the proper sequence, an RC circuit 262 eliminates any noise and a latch 264 is reset. The latch circuit 264 may be of the same type of latch circuit described above and specifically may be one of the latch circuits contained on an RCA type CD 4043 integrated circuit. The output of the latch passes through an inverter 266 for application to a NAND gate 268. The output of the NAND gate 268 is one of the inputs to the NAND gate 260.

The set input of the latch 264 is controlled from the reset or stop operate logic block H. Specifically, circuitry of block H includes a NAND gate 270 which receives three inputs representing conditions which determine when the latch 264 of circuit block F is to be set.

The output from the NAND gate 260 is applied to a second NAND gate 272 and the output of this NAND gate 272 is the motor drive signal. The NAND gate 272 provides the motor drive signal in accordance with the operation of the slew control block A, the operation of which will be described at a later portion of this specification.

The output from the NAND gate 272 is also coupled to the divide-by-96 circuit block B shown in FIG. 9. The circuit of block B includes a pair of counter dividers 274 and 276. The first counter divider 274 provides a division by 6 and the second counter divider 276 provides a division by 16. The combination of these dividers provides a division by 96 and in the pump of the present invention, 96 motor drive pulses represents the delivery of 1 cc of fluid.

The divider 274 may be provided by using the appropriate output of a divide-by-8 circuit. For example, the divider 274 may be a four stage divide-by-eight Johnson counter of the type described above which may be an RCA type CD 4022. The CE input is a clock enable input and this input is provided by the output of a divider enable NAND gate 278. The inputs to the NAND gate 278 are forward signal and the not-load signal representing the pump operating in the forward direction and not loading the cassette.

The outputs from the divider 274 are provided as the set and reset inputs to a latch circuit 280 which may be of the conventional type described above. The latch 280 is set and reset in accordance with the divider 274 counting from zero up to 6 pulses on an alternate basis. The latch 280 is used to provide for a clearing and resetting of the divider 274 after each count of six clock pulses. Specifically, the output of the latch 280 is coupled through an inverter 282 to a NAND gate 284 so as to provide for a reset signal to the divider 274 in accordance with the NAND gate receiving a not-power-on reset signal and the output signal from the inverter 282.

One of the output signals from the divider 274 is coupled to the divider 276 as a clock input and for each six pulses received by the divider 274, the divider 276 receives one pulse. The divider 276 may be of a binary counter of the type described above as represented by RCA type CD 4029. The carry-out signal from the divider 276 is used as the output signal and occurs one for each sixteen input pulses to the divider 276. The output from the divider 276 is applied to block C which is the driver for the predetermined counter which counter is included in block DD.

The output from the divide-by-96 circuit block B is coupled through a capacitor 286 and to a resistor 290 as a differentiated input to an inverter 288. The resistor 290 also provides the proper biasing of the input signal to the inverter 288. The output from the inverter 288 is coupled through a resistor 292 to the base of a driver transistor 294. A diode 296 decouples the inductive spike at the collector of the transistor 294.

The output of the transistor 294 is coupled to the predetermined counter DD which includes the volume-to-be-infused dial 54 shown in Block DD. The counter is set by the operator of the pump at the face of the pump by adjusting the knobs of the dial 54 to the total number of cubic centimeters of fluid to be administered to the patient. Each time the divide-by-96 circuit shown in block B counts 96 motor pulses, the predetermined counter is counted down one digit, representing one cc of fluid administered to a patient and the indicators of the dial 54 are reduced by one digit. When the counter reaches zero, a switch 298 closes to provide an output signal from the counter block DD.

Returning now to block A shown in FIG. 8 which is the slew control. The circuitry of block A is used to provide signals which ultimately control the speed at which the motor is driven. For example, during the purge mode of the pump, the motor is driven rapidly in both the forward and reverse directions to rapidly fill the cassette and then rapidly pump the fluid from the cassette to purge the lines. During the normal operation of the pump, the motor is driven in a forward direction at a preselected rate for the administration of the fluid as controlled by the preselected positions of the switches 226, 228 and 230 which are part of the rate dial 56.

The motor drive pulses, at the proper rate, are one of the three inputs to the NAND gate 260. The other inputs to the NAND gate 260 are a signal representing the motor in the forward direction, and an output from the start/operate latch block F representing the operation of the operate switch 62. The output from the NAND gate 260 is applied to the NAND gate 272 and the output from the NAND gate 272 is the motor drive signal when the pump is operated in the normal operate mode.

The purge switch 58 is normally in the open position unless operated by pushing the switch 58 to provide the switch to be in the purge or load position. When the switch 58 is in the purge position, this provides one input to a NAND gate 300. The other inputs to the NAND gate come from NAND gates 302 and 304. The NAND gate 304 is controlled by the load and not-load signals since a first input to the NAND gate 304 is the load signal as passed through an inverter 306. The second input to the NAND gate 304 is the output signal from a latch 308 as passed through an inverter 310 to the NAND gate 304. The set input to the latch 308 is the not-load signal. This portion of the circuit insures that the purge signal is not passed through the NAND gate 300 unless the pump is not in the load mode. A forward stop signal representing the situation when the motor is to go into a reverse drive to refill the cassette is used to reset the latch 308. A pair of resistors 312 and 314 are connected to a supply voltage to bias the purge and load signals.

The output of the NAND gate 300 is used as a data input to the flip-flop 316 and this flip-flop may be one of a dual data type flip-flop of a conventional type such as RCA type CD 4013. The level of the signal of the data input is transferred to the "Q" output during the positive-going transition of the clock signal. A clock input to the flip-flop 316 is provided from the Q output of a second flip-flop 318 of a similar type. The flip-flop 318 is controlled by the reference oscillator signal produced by the oscillator shown in block D. The Q output from the flip-flop 316 is used as one input to a NAND gate 320. The other input to the NAND gate 320 is the Q output from the flip-flop 318. The output from the NAND gate 320 is used as the second input to the NAND gate 372 to provide the motor drive output signal from the NAND gate 272.

Figure 11:
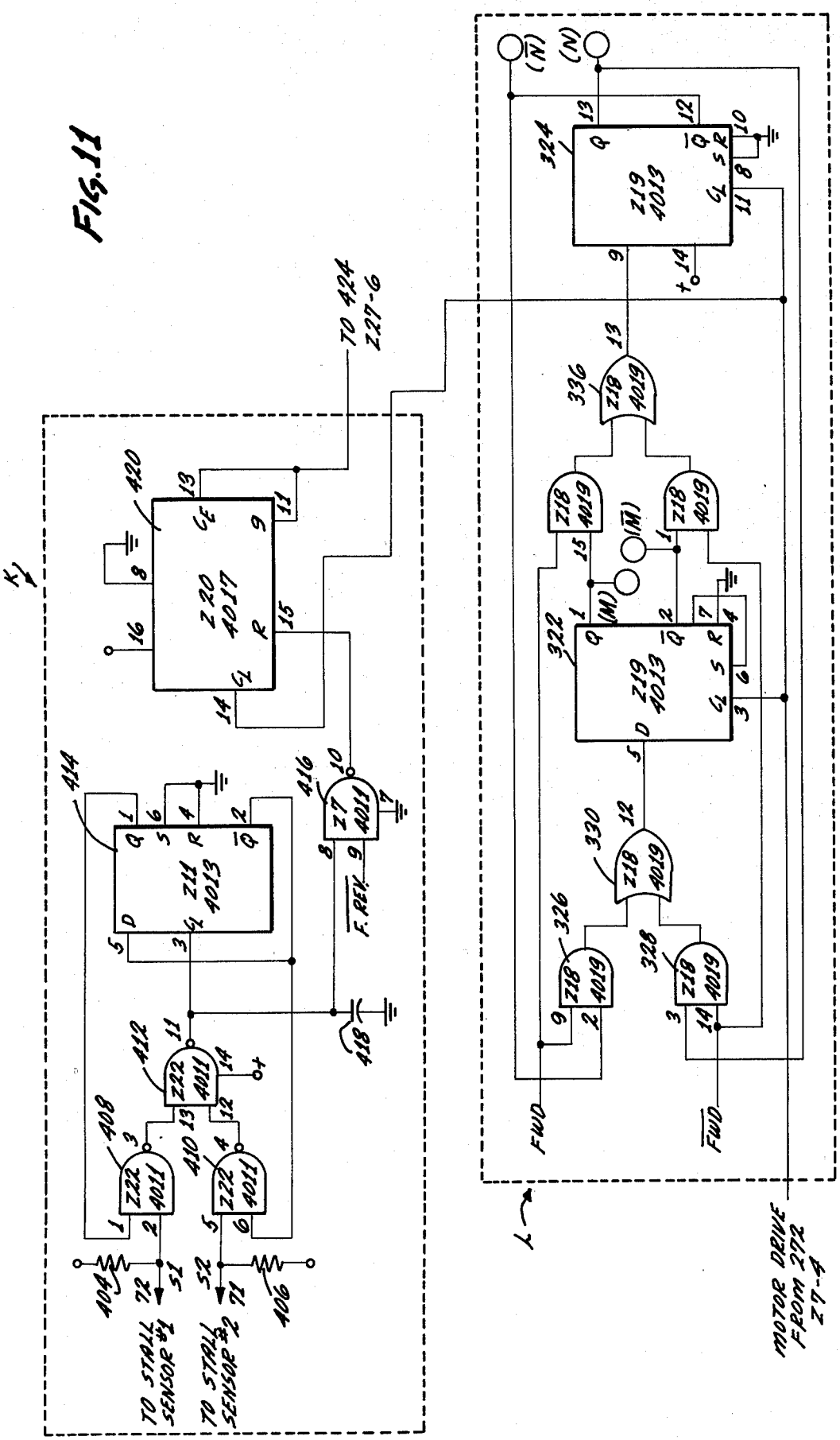

The motor drive output signal from block M is applied as an input signal to block L shown in FIG. 11 which is the stepping motor drive logic circuit. Specifically, the motor drive output signal is applied as a clock input signal to a pair of flip-flops 322 and 324. The flip-flops 322 and 324 may be data type flip-flops wherein the level of the signal at the data input is transferred to the Q output during the positive-going transition of the clocking signal. Both flip-flops 322 and 324 may be contained on a digital integrated circuit of the type such as RCA type CD 4013.

The forward and not-forward signals are applied as inputs to AND gates 326 and 328 and with the output from the AND gates applied to an OR gate 330. The combination of AND gates 326 and 328 and OR gate 330 form an and/or select gate and the three gates may be part of a digital integrated circuit such as an RCA type CD 4019. The outputs from the flip-flop 324 which are labeled N and $\overline{N}$ are also applied as inputs to the AND gates 326 and 328. The input to the flip-flop 322 is therefore a signal representing either the forward or not-forward condition for the motor drive.

The forward and not-forward signals are also applied to a pair of AND gates 332 and 334, the output of which are applied to an OR gate 336. The AND gate 332 and 334 and OR gate 336 form an and/or select gate identical to the one described above and which may be part of an integrated circuit of an RCA type CD 4019. The other inputs to the AND gates 332 and 334 are the outputs from the flip-flop 322 and these outputs are labeled M and $\overline{M}$.

The four output signals M and $\overline{M}$ and N and $\overline{N}$ are used as the input signals to the stepping motor driver block O shown in FIG. 15 and specifically are used to provide the driving of the stepping motor 84 in the proper direction and at the proper speed.

It can be seen in FIG. 15 that the stepping motor driver block O uses the signals N and $\overline{N}$ and M and $\overline{M}$ as input signals to a plurality of NAND gates 338 through 344. The four NAND gates 338 through 344 may all be part of an integrated circuit such as an RCA type CD 4011. The other input to the NAND gates 338 through 344 is an output signal from the over rate detection circuit block E shown in FIG. 12.

The outputs from the NAND gates 338 through 344 are coupled through inverters 346 through 352 to a plurality of transistors 354 through 360. The output from the transistors 354 through 360 are coupled as a plurality of inputs to the stepping motor 84 so as to provide for driving the stepping motor in particular directions and at particular speeds in accordance with the input signals. The stepping motor may be of a conventional type and as an example may be a stepping motor manufactured by Hayden Mfg. Corp. as a type R86201.

The coupling of the output signals from the inverters 346 to 352 to the transistors 354 through 360 is provided through resistors 362 through 368. The power supply to the transistors 354 through 360 is provided from a source of positive voltage and through a resistor diode combination for each transistor which resistor diode combinations are designated 370 through 376. The transistor 360 also receives as an input an output signal coupled through a resistor 378 from the over rate detection circuit block E shown in FIG. 12.

The over rate detection circuit shown in block E includes input signals representing the rate of infusion of the fluid which rate is set by the dial 56 on the front panel of the pump. Specifically, the input signals are taken from the binary coded counters 220, 222 and 224 and represent the most significant digit of the ones, all of the digits for the tens, and the two digits used for the hundreds. This provides for a total of seven input signals which are summed using a plurality of seven diodes collectively designated as 380 and a plurality of seven resistors collectively designated as 382. An output signal is formed having a voltage representative of the rate which has been preset by the operator of the pump. The output signal from the summing network is coupled across a voltage biased RC circuit 384 and through an inverter 386 to form one input signal to transistor 360 shown in block O in FIG. 15.

The motor drive signal from Block A is coupled through a diode 388 and an RC circuit 390 including a pair of resistors and a capacitor to an inverter 392. The output from the inverter is coupled through a resistor 394 for summing with the electrical input from the dial 56. A pair of diodes 396 and 398 are used to isolate the motor drive signal from the electrical input information which has been preset in the dial 56.

The motor drive signal is also coupled through an inverter 400 to an NAND gate 402 and with the not-full on signal used as a second input to the NAND gate. The output from the NAND gate 402 which represents the motor drive pulses is also used as an input to the NAND gates 338 through 344 shown in block O. The signal from the NAND gate 402 is also passed through the diode 398 to the summing point. As long as the motor drive pulses are not over-rate by a particular amount, the output signal from the inverter 386 does not represent an over-rate condition.

Block K shown in FIG. 11 is the motor stall detector circuit and provides a comparion of the motor drive pulse rate with the actual speed of the stepping motor 84. Specifically, the pair of stall sensors 92 and 94 shown in FIGS. 2 and 21 provide input signals across resistors 404 and 406 to NAND gates 408 and 410. The output from the NAND gates 408 and 410 as applied to a NAND gate 412 and the output from the NAND gate 412 is in accordance with the rate at which the motor is driving the pump. The output from the NAND gate 412 is applied to a flip-flop 414 and is used as the clock input to the flip-flop 414. Flip-flop 414 may be of the type described before and specifically may be an RCA type CD 4013. The Q and $\overline{Q}$ outputs from the flip-flop 414 are applied as second inputs to the NAND gates 408 and 410. The $\overline{Q}$ output from the flip-flop 414 is also used as the data input to the same flip-flop.

The output from the NAND gate 412 is also applied across a capacitor 418 as an input to a NAND gate 416. The second input to the NAND gate 416 is from the block R shown in FIG. 22, which is the forward-reverse logic circuit. The output from the NAND gate 416 is applied as a reset signal to a counter-divider 420. The motor drive pulse signal to a counter-divider 420. The motor drive pulse signal is applied to the counter-divider 420 as a clock signal. The counter-divider 420 may be a five stage Johnson decade counter which is used as a comparator between the reset input and the clock input. Specifically, the counter-divider 420 may be a digital integrated circuit of the type such as RCA type CD 4017.

The motor drive pulse signal used as a clock input to the counter-divider 420 provides for the counter-divider to count one count for each positive clock transistion provided by the motor drive pulse signal as long as the clock enable input is low. It can be seen that one of the counter outputs is applied to the clock enable input. If the counter continues to count up to the value provided by the counter output, then the clock enable goes high to indicate that the motor is in a stall condition. If however, the output from the NAND gate 416 occurs on a periodic basis to reset the counter 420, then the output from the counter 420 never goes high, thereby indicating the motor is operating properly and not in a stall condition. The block K is essentially an electrical mechanical comparator since the signals from the stall sensors relate to the actual motion of the shaft of the motor 84, as detected by the stall sensors, and with this mechanical motion compared with the electrical pulse signal used to drive the motor 84. The output from the counter 420 is used as an input to the latch for fault and sensor outputs circuit block P shown in FIG. 18.

Figure 18:
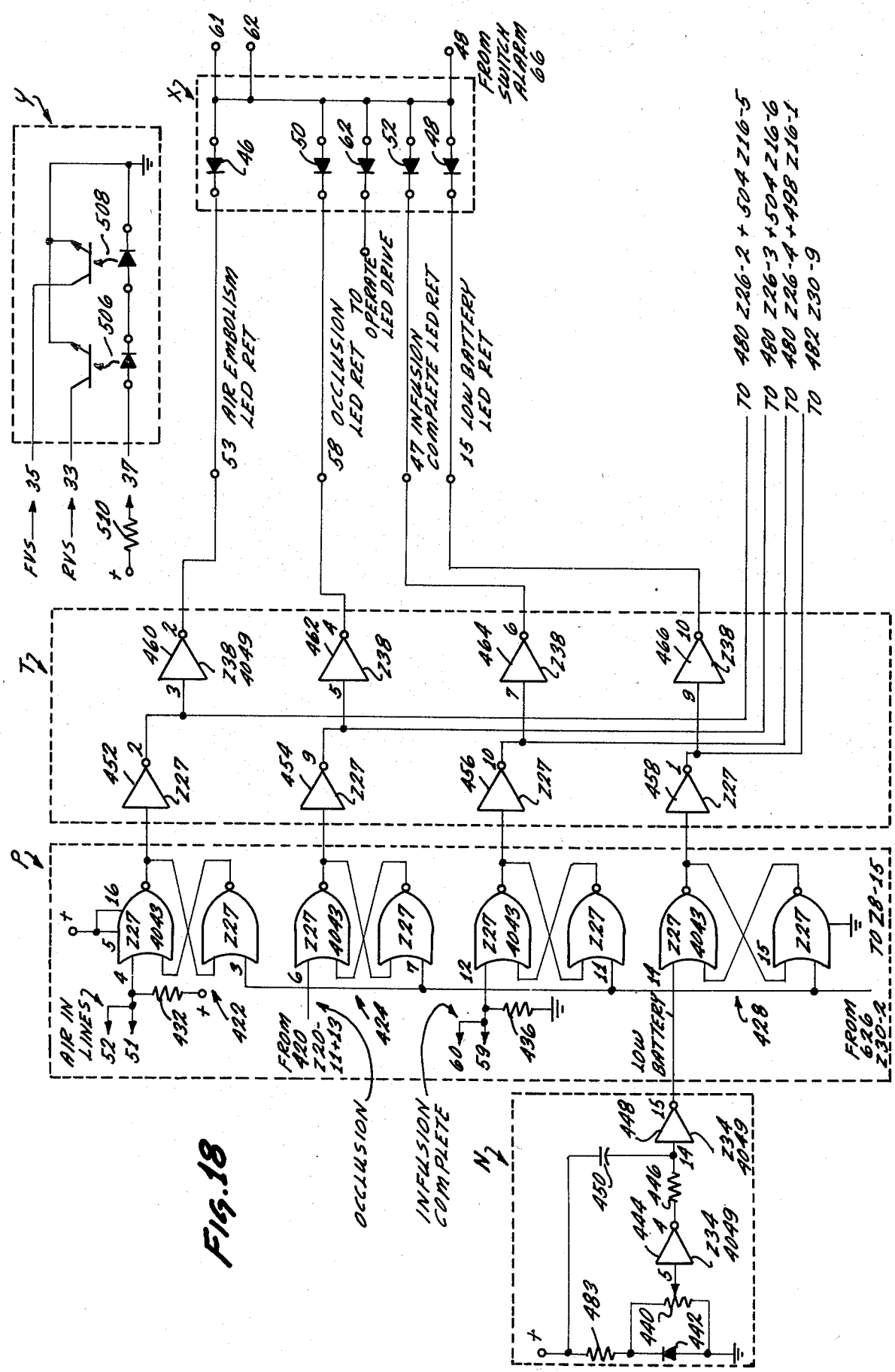

The block P shown in FIG. 18 which is the latch for fault and sensor outputs is shown to receive a plurality of input signals representing various fault and alarm conditions. The block P includes four latch circuits 422, 424, 426, and 428. These latch circuits may all be part of a single integrated circuit such as an RCA type CD 4043.

The latch 422 receives as an input signal the output from the air-in-line sensors which are formed by light emitters 98 and 100 and photodetectors 102 and 104 shown in block U, in FIG. 21 and in FIGS. 5 and 6. The light emitters receive supply current from a source of positive voltage through a resistor 430. The output from the photodetectors 102 and 104 are coupled in series and applied to the latch 422 across a resistor 432.

The input to the latch 424 is, as indicated above, from the motor stall detector circuit block K and is a signal representative of the motor in a stall condition which would normally represent an occlusion of the fluid line. The input to the block K is from the stall sensors 92 and 94 which provide output signals in parallel. The light emitter portion of the stall sensors receive electrical supply from a source of positive voltage through a resistor 434.

The latch 426 receives an input signal from the predetermined counter 54 shown in block DD representing the infusion of fluid complete. Specifically, the switch 298 shown in FIG. 9 closes when the counter 54 reaches a zero reading. At that time, the output signal from the counter 54 is applied to the latch 426 across a resistor 436.

Finally, the latch 428 receives an input signal representing a low battery signal from the low battery detector block N shown in FIG. 18. The low battery detector block N detects when the voltage level of the battery is below a certain predetermined value. Specifically, the battery voltage is applied across a voltage divider including a resistor 438 and a potentiometer 440 and with a zener diode 442 coupled in parallel across the potentiometer 440. The output of the potentiometer 440, taken from the arm of the potentiometer, provides for a threshold adjustment and with this output signal coupled through an inverter 444 and a resistor 446 and applied as an input signal to a second inverter 448. A capacitor 450 is also coupled between the battery voltage and the input to the inverter 448. The output of the inverter 448 is a signal representative of the voltage level of the battery and when the level of the battery falls below a predetermined level, as determined by the position of the adjustable arm of the potentiometer 440, the low battery detector shown in block N provides a signal to control the latch 428 shown in block P.

The output from the latches 422 through 428 shown in block P are supplied to the fault and indicator control block T shown in FIGS. 18 and 19. The circuitry of block T includes a plurality of inverters 452 through 458 which supply output signals to the nurses call relay driver block W shown in FIG. 19. The portion of block T shown in FIG. 19 also includes logic circuitry to provide output signals representative of the finish of the delivery of the predetermined quantity of fluid and to control a minimum delivery of fluid thereafter.

In the portion of block T shown in FIG. 18, the output from the inverters 452 through 458 are coupled to a plurality of inverters 460 through 466. The output of these inverters are used to drive the LEDs 46, 48, 50 and 52 representing the output indicators on the front panel of the pump and designated at block X in FIG. 18.

The actual power to the LEDs 46 through 52 and an operate LED 62, all shown in block X, is provided by the LED and audible timer circuit block M and the LED driver block V both shown in FIG. 17. Specifically, in the circuitry of block M, a pulse signal having a fast rate is supplied to a divider 468 and this pulse signal may be supplied from the divider 224 shown in Block I as the first rate stage signal. The divider 468 may be, for example, a four stage divide-by-eight Johnson counter such as the type provided by an RCA type CD 4022. Particular outputs from the divider 468 are used so that the pulse signal applied to the divider are counted down and with these output signals coupled to NOR gates 470 and 472. For example, NOR gate 472 receives signals representing the zero output and the four output while NOR gate 470 receives inputs representing the zero output, the two output, and the five output. The outputs from the NOR gates 470 and 472 are therefore pulse signals at a lower rate than the input signal to the divider 468.

The output from the NOR gate 472 is applied through a resistor 474 to a transistor 476 which form block V. The transistor 476 supplies an alternating potential to drive the LEDs shown in block X and also to drive the audible horn 64 when the switch 66 is in the closed position as shown in FIG. 19. The output from the NOR gate 470 is coupled as one input to a NOR gate 478 and with the other input to the NOR gate 478 being the input to the divider 468. The output from the NOR gate 478 is coupled as one input to the NAND gate 256 shown in block J. The LEDs shown in the block X are driven with a flash rate and with the audible alarm having a beep rate in accordance with the pulse rate of the output signal from the transistor 476 shown in block V.

Block W shown in FIG. 19, which is the nurse call relay driver, receives as inputs all of the alarm conditions from the block T and with these inputs applied to a NOR gate 480 and an inverter 482. Specifically, only the low battery fault condition is supplied to the inverter 482 while the other fault signals are supplied to the NOR gate 480. The outputs of the NOR gate 480 and the inverter 482 are applied as inputs to a NAND gate 484. It can be seen that aside from the low battery signal, the other fault conditions which are coupled from the NOR gate 480 are used to provide a not-fault signal which is used as an input signal to the NAND gate 270 which is part of the reset or stop logic block H, shown in FIG. 8. If a fault occurs, the pump is therefore stopped. If the low battery condition is allowed to continue for a sufficient period of time without recharging the battery, then there will be insufficient power to drive the pump and this has the effect of stalling the motor 84. This is detected by the stall sensors so that the NOR gate 480 produces the signal to control the reset stop logic block H to stop the pump when there is insufficient power from the battery.

The output from the NAND gate 484 is applied to a pair of inverters 486 and 488 in parallel to control a nurse call relay 490 and the audible alarm 84. The relay 490 receives power from a source of positive voltage through a diode 492. The audible alarm 64 is coupled to the block W through a resistor 494 and a diode 496. When any of the alarm conditions occur, the nurse call relay 490 is activated to provide an output signal to the nurse call jack 68 and if the switch 66 is closed, the audible alarm is sounded in addition to activating the appropriate one of the LEDs shown in block X.

As shown in the portion of block T shown in FIG. 19, the alarm signals and specifically, the signals representing infusion complete, air-in-line, and occlusion are used to provide for a finish delivery signal and a not-minimum delivery signal. Specifically, when the infusion is complete, a signal is applied to a NOR gate 598 which provides an output signal through an inverter 500 to a NAND gate 502. The output from the inverter 500 is the finish delivery signal. The two alarm signals representing air-in-line and occlusion are coupled to a NOR gate 504 which also provides an input signal to NAND gate 502. The output from the NAND gate 502 is the not-minimum delivery signal and it will be appreciated that as explained above, after the delivery of the predetermined quantity of fluid is complete, the pump provides for a minimum delivery at a very low rate such as one cc per hour. However, it is not desirable to provide this minimum delivery unless neither of the fault conditions representing air-in-line or occlusion is present.

The block X representing the LEDs on the front panel of the pump also includes an LED which provides for a light in the operate button 62 when the pump is operating. As shown in FIG. 20, a not-on signal is coupled through an inverter 506 to provide for the on signal. In addition, the output from the inverter 506 is coupled through an inverter 508 to produce a signal from a resistor 510 to control the operation of the LED 62 portion of the LED and the operate button 62 shown in block X.

Figure 22:
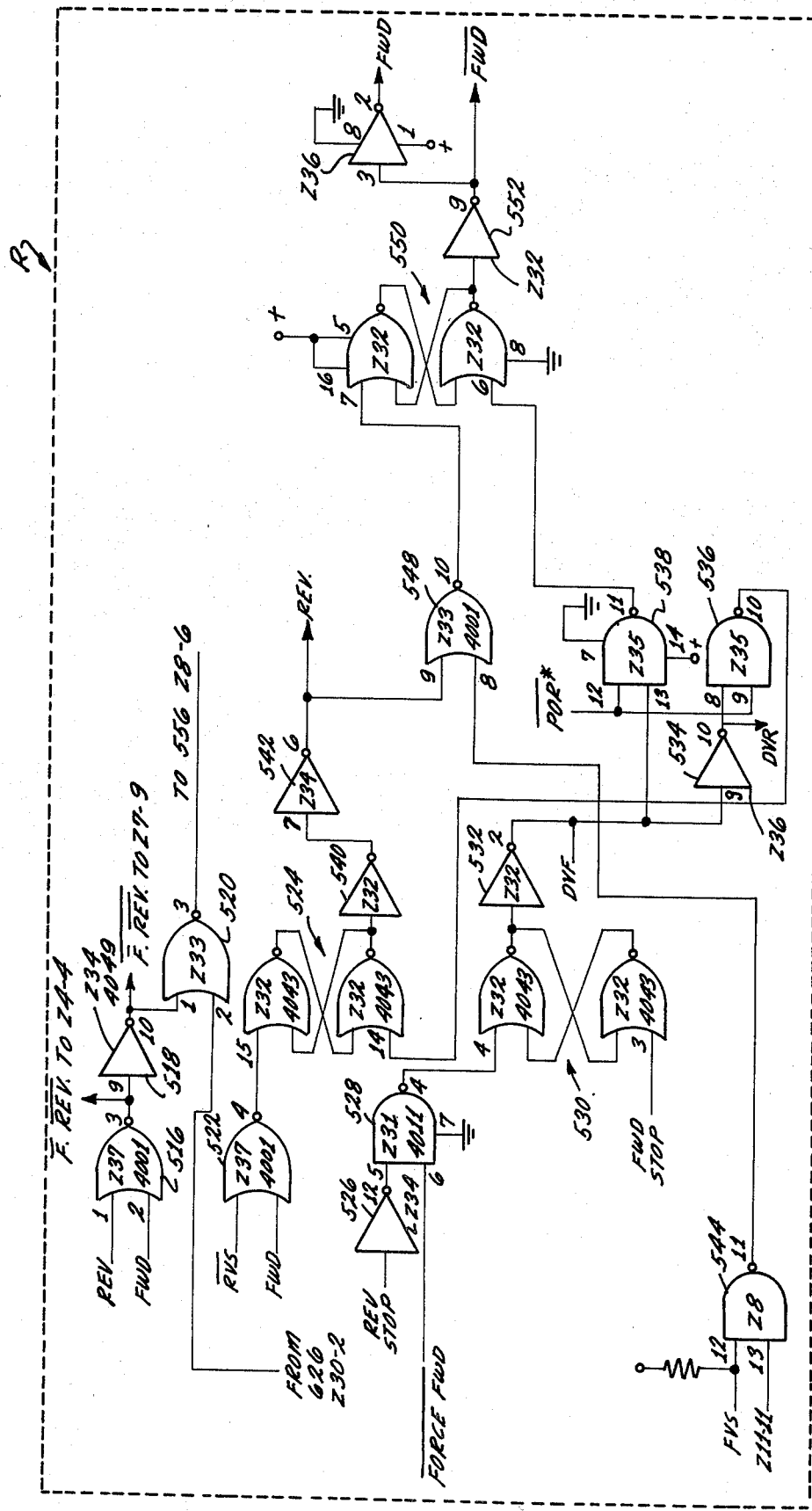

Block R shown in FIG. 22, which is the forward reverse logic, is responsible for determining the direction of rotation of the DC motor 74 which operates the value control member 36 shown in FIG. 2. The member 36 controls the operation of the valve 38 of the cassette 24 shown in FIG. 3. A pair of light detectors 506 and 508 form block Y shown in FIG. 18 and the detectors 506 and 508 are also shown in FIG. 2. The detectors 506 and 508 provide output signals representative of the forward valve stop position and the reverse valve stop position. A source of power supply is coupled to a resistor 510 to supply power to the light emitting portions of the light detectors 506 and 508.

A disc member 512 having a slot 514, as shown in FIG. 2, may be used in combination with the light detectors 506 and 508 to provide for the output signals representing the positions of the valve 38. The signals from the light detectors 506 and 508 and their logical opposites plus other signals developed in the electronic portion of the system shown in FIGS. 8 through 24 are used as various inputs to the forward reverse logic block R. Specifically, the reverse and forward signals are applied to a NOR gate 516 to provide an output signal used as an input to the flip-flop 316 which is part of the block A shown in FIG. 8. The output from Nor gate 516 is passed through an inverter 518 to provide an input signal to a NOR gate 520 and also to provide a signal used as an input to the NAND gate 416 shown in block K which is the motor stall detector circuit.

The not-RVS signal and the forward signal are used an input signals to a NOR gate 522 and with the output of the NOR gate 522 used as a reset signal for latch circuit 524.

The reverse stop signal is applied through an inverter 526 as an input to NAND gate 528 and the not-force forward signal is applied as an input to the NAND gate 528. The output from the NAND gate 528 is used as a set input to a latch 530 and with the forward stop signal used as a reset input to the latch 530. The output from the latch 530 passes through an inverter 532 to produce the drive valve forward signal and the output from the inverter 532 is passed through a second inverter 534 to be the drive valve reverse signal.

The output of the inverter 534 is also used as an input to a NAND gate 536. The output from the inverter 532 is used directly as an input to a NAND gate 538. The not-power on reset signal is used as a second input to NAND gates 536 and 538. The output from the NAND gate 536 is used as the reset input for the latch 524. The output from the latch 524 is passed through a pair of inverters 540 and 542 to produce the reverse signal.

The forward valve stop signal and the clock signal from flip-flop 254 shown in block J are applied as inputs to NAND gate 544. A resistor 546 supplies positive voltage to the NAND gate 544 at the same input position as the forward valve stop signal. The output from the NAND gate 544 is applied as one input to a NOR gate 548 and the reverse signal from inverter 542 is applied as the second input to the NOR gate 548. The output from the NOR gate 548 is used as a reset input to a latch 550. The set input to the latch 550 is from the NAND gate 538. The output from the latch 550 is passed through an inverter 552 to provide the not-forward signal and through a second inverter 554 to provide the forward signal.

Figure 24:
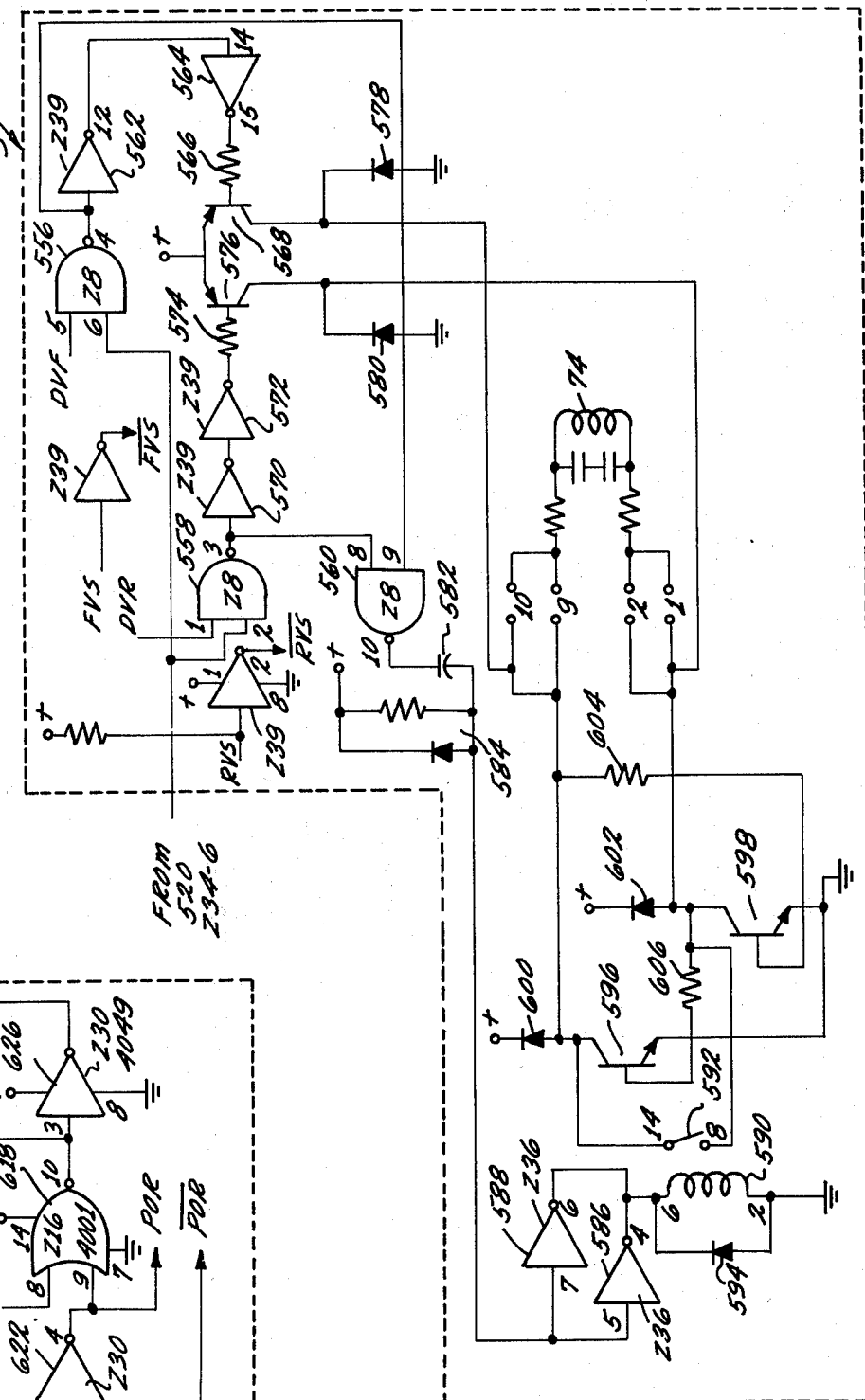

Block S shown in FIG. 24 represents the DC motor control logic and drive circuit to control the DC motor 74 which operates the valve 38 within the cassette. The drive valve forward signal and the drive valve reverse signal from block R shown in FIG. 22 are used as inputs to NAND gates 556 and 558. The other input to the NAND gates 556 and 558 is from the NOR gate 520 in block R. The output of NAND gate 556 is coupled directly to NAND gate 560 and is coupled through a pair of inverters 562 and 564 and a resistor 556 to the base of a transistor 568. The output of NAND gate 558 is used as the other input to the NAND gate 560 and is applied through a pair of inverters 570 and 572 and a resistor 574 to the base of a transistor 576. The collectors of the transistors 568 and 576 are coupled through diodes 578 and 580 to ground and the outputs across the diodes 578 and 580 are used as input signals to the DC motor 74.

The output from the NAND gate 560 is coupled through a capacitor 582 and across a parallel resistor diode circuit 584 to a pair of inverters 586 and 588 which are also in parallel. The output of the inverters 586 and 588 is used to drive a solenoid winding 590 to control a switch 592 which provides dynamic braking to the DC motor. A diode 594 is coupled across the solenoid winding 590. A pair of transistors 596 and 598 are also used to control the DC motor 74 and specifically to control the direction of rotation of the motor 74. The rotation of the motor 74 in turn controls the position of the valve 38 in the cassette 24.

The collector of the transistors 596 and 598 are coupled through diodes 600 and 602 to a source of positive voltage. The base of transistor 598 is coupled through a resistor 604 to the collector of transistor 596 and alternately the base of transistor 596 is coupled through a resistor 606 to the collector of transistor 598. When the transistor 568 is conducting in response to a valve drive signal in a first direction, then transistor 598 will conduct to complete the current path while transistor 596 will be turned off. The reverse situation occurs when transistor 576 is conductive in response to a valve drive signal in a second direction. The solenoid 590 is used to provide dynamic braking to the DC motor 74.

The forward stop and reverse stop light detectors 150 and 152 are used to provide the forward stop and reverse stop signals used in block R shown in FIG. 22 and these light detectors are also designated as a second portion of block R shown in FIG. 21. A resistor 608 is used to supply power to the light emitter portion of the light detectors 150 and 152. The output from the light detectors 150 and 152 are in parallel and are supplied to a pair of resistors 610 and 612 shown in FIG. 14 and which resistors are coupled to a source of positive voltage. The output across the resistor 610 is coupled through a pair of NAND gates 614 and 616 to produce the forward stop signal.

Figure 23:
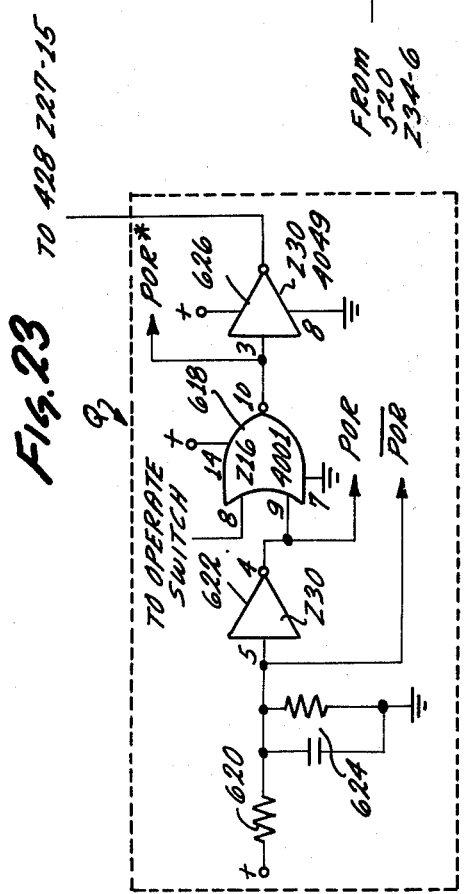

In order to provide for the power on reset signal used in various portions of the system shown in FIGS. 8 through 24, the block Q shown in FIG. 23 is used. The output from the operate switch is used as one input to a NOR gate 618. The second input to the NOR gate 618 is from the source of positive voltage as applied through a resistor 620 and an inverter 622. The input to the inverter 622 is taken across a resistor capacitor parallel combination 624. The output from the inverter 622 is the POR signal and the output representing the not-POR signal is the signal used as an input to the inverter 622. The output from the NOR gate 618 is a not-POR* signal and this signal as inverted by the inverter 626 is the POR* signal. The POR signal is used as the reset input to the latch circuits in block P.

The battery charger 628 shown in FIG. 13 as block AA is coupled through a line plug to the 110 line voltage. The battery charger 628 may be of any conventional type and the output of the battery charger is coupled to the plug 70 at the rear of the pump to supply charging current to the battery 630. The battery 630 is the main source of power for the pump. A fuse 632 is used to fuse the charging of the battery and the switch 60 on the front panel of the pump is used to control the application of battery supply voltage to the various circuits within the pump.

In the general operation of the pump, the initiation of the operation of the pump occurs by turning the power on using the switch 60 shown in block AA which is the battery charger on-off circuit. When the power is turned on, the power on reset block Q provides the signals to reset all the circuits within the pump so that the pump is ready for the loading of a cassette 24. When a cassette 24 is loaded, the reset dial 56 including the switches 226, 228 and 230 are all set to zero. This zero condition is represented by the output signal from the NAND gate 244 which receives as its input signals, output signal from the NOR gates 238, 240 and 242.

The output signal from the NAND gate 244 is used to enable the load purge switch 58 so that the load purge switch does not provide for operation without the output signal from the NAND gate 244.

The directional slew control circuit block A is used to control the motor drive logic circuit block L to provide output signals which represent the proper direction and the proper speed for the motor 84. These output signals from the block L are coupled to the stepping motor driver block O and then on to block Z which is the stepping motor 84.

After the lines to the pump and to the patient are purged, the operator of the pump sets into the rate dial 56 shown in block BB, the desired rate of infusion. The decade rate scaler shown in block I provides output pulses in accordance with the desired rate of infusion, and with the decade rate scaler driven from oscillator shown in block D and through the pulse width control block G. Specifically, the pulses provided as the input to the decade rate scaler block I are counted down and dependent upon the particular points set by the rate dial 58 and specifically the switches 226, 228 and 230 the decade rate scaler select decoding points to produce pulses which relate to one pulse equal to one ninety-sixth of a cc and with the rate of these pulses in accordance with desired rate of infusion.

The predetermined counter 54 shown in block DD is also set to the desired total volume of fluid to be infused. At this time, the plunger in the cassette is being driven up to infuse fluid into the patient, and with the position of the plugner at its upward extremity and downward extremity detected by the light sensors shown in block R. The forward and reverse stop points are ultimately provided to block A to decode the direction of the drive for the motor. As the motor drive pulses are used to drive the motor 84, these pulses are also accumulated by the divide-by-96 circuit, block B. Each time 96 pulses are counted, one pulse is sent to the driver for the predetermined counter block B which is used to count the predetermined counter block DD down one count. When the predetermined counter 54 shown in block DD counts down to zero, this indicates that the volume of fluid infused is complete and instead of stopping the pump completely, the pump is put into a keep-open rate of one cc per hour.

The motor shall detector circuit block K is also accumulating motor drive pulses and is also receiving pulse signals relating to the actual rotation of the motor shaft, so as to detect an occlusion in the line or a stalled motor. When either of these conditions occurs, the pump is turned off. Specifically, the disc on the stepper motor includes an encoder wheel having six slots so that the number of pulses required to advance the motor one-sixth of a revolution is compared with the actual revolution of the encoder wheel as detected by the stall sensors 92 and 94. If the motor is stalled, or if an occlusion occurs so that the motor can not drive the pump, block K receives more motor drive pulses than desired before the next slot is detected and at that time, the pump is turned off and the occlusion alarm is activated.

Among the other alarm conditions are an air embolism alarm, which detects for the presence of air in the line to reactivate the pump and to activate the alarm. In addition, the low battery and infusion complete alarms are controlled in the manner described above.

The reverse time rate compensation circuit block J compensates for the loss of accuracy that would occur because of the period of time during which the plunger is returned to the bottom position so as to fill the cassette 24. Generally, this period of time is about 5 seconds and at higher rates of infusion, this period could represent a considerable loss of pulses to drive the motor which would provide for a loss in accuracy in the infusion rate. The circuit shown in block J accumulates any motor drive pulses that are produced during the refill time for the cassette and then these pulses are slowly added back along with the normal motor drive pulses. For some period the rate is therefore slightly more than is being generated by the decade rate scaler shown in block I. The circuitry of block J therefore provides for a slow administration of additional fluid across a time period to compensate for the loss of accuracy because of the refill time for the cassette.

The forward reverse logic block R produces signals to control the forward and reverse operation of the motor 74 which motor controls the valve 38 within the cassette 24. This valve must be controlled to be in a first position during the infusion of fluid into a patient and in a second position during the refill of the cassette after the plunger has emptied the cassette.

The various circuits which form the blocks shown in FIG. 7 have been described in detail with reference to FIGS. 8 through 24. In addition, it will be noted that many of the logic gates, flip-flops, counters, etc., include additional reference characters other than those described above. Specifically, these reference characters are those starting with Z such as Z12, 18, 32, etc., which refer to a particular integrated circuit. For example, as shown in Block L in FIG. 11, a total of four AND gates and two OR gates all include the reference character Z18. This identifies all of these gates as being present in the same integrated circuit. A second reference character which is sometimes present, is a four-digit number such as 4019 shown in the AND and OR gates marked "Z18". This reference character refers to a specific type of integrated circuit commercially available from RCA as the CD series and the reference character 4019 refers to an RCA type CD 4019. Although it is appreciated that other companies manufacture similar conventional integrated circuit, the RCA types are used throughout as a convenient standard in describing the application. For example, in block L, a pair of flip-flops 322 and 324 are both marked Z19 and the four-digit number 4013. This indicated that both flip-flops 322 and 324 are part of the same integrated circuit characterized by Z19 and that it is an RCA type CD 4013. The other numbers and letters shown adjacent to the specific input and output lines such as in flip-flop 322 refer to standard input and output lead designating designations used in the RCA type integrated circuits.

It is to be appreciated that these conventional designations are shown merely to provide clarification as to the specific operation of the invention, and that the invention is not to be limited to these specifics. Although the invention has been described with reference to a particular embodiment, it is to be appreciated that other adaptations and modifications may be made and the invention is only to be limited by the appended claims.

We claim:

1. A volumetric pump for pumping between a patient and a source a volume of fluid at a preselected controlled rate until a preselected volume of fluid has been pumped, including
    an output line,
    volumetric means for receiving the volume of fluid from the source and providing the fluid to the output line,
    the volumetric means including a chamber of a predetermined volume per increment of displacement which predetermined volume is a fraction of the volume of fluid from the source and a fraction of the fluid to be pumped to the output line,
    a plunger movable within the chamber on an incremental basis in a first direction for filling the chamber and movable within the chamber, in a second direction opposite to the first direction, on an incremental basis for emptying the chamber,
    plunger means coupled to the plunger for driving the plunger on the incremental basis in the first direction to fill the chamber and for driving the plunger on an incremental basis in the second direction to empty the chamber,
    a stepper motor constructed to operate in increments each representative of a particular distance,
    control means, including the stepper motor, operatively coupled to the plunger driving means to obtain an incremental operation of the plunger driving means for driving the plunger on the incremental basis in the first direction and to obtain an incremental operation of the plunger driving means for driving the plunger on an incremental basis in the second direction,
    means for providing an indication representing the preselected amount of fluid to be supplied between the patient and the source,
    means responsive to the incremental operation of the plunger driver means in driving the plunger on an incremental basis in the second direction for counting the number of such incremental operations to obtain a determination of the amount of fluid transferred between the source and the patient, and
    means responsive to the count of the incremental operations representing the determination of the amount of fluid transferred between the patient and the source for interrupting the supply of the fluid between the patient and the source when the amount of such fluid corresponds to a preselected incremental count.

2. The volumetric pump of claim 1 additionally including means included in the control means for obtaining an operation of the plunger driving means through the particular count of the incremental operations of the stepper motor to provide a precise control of the preselected volume of fluid pumped between the patient and the source.

3. The volumetric pump of claim 2 wherein alarm means are provided and means are included for detecting air in the output line from the volumetric means and for activating the alarm means upon such detection and where means are included for automatically interrupting the pumping of fluid upon such detection.

4. The volumetric pump of claim 3 wherein the means to detect the air in the output line from the volumetric means includes light emitter means to direct light toward the output line from the volumetric means and light detector mean to detect changes in the light passing through the output line from the volumetric means in accordance with the presence of air in the output line and wherein the light detector means is disposed relative to the light emitting means to receive light refracted by air in the output line and wherein the alarm means are responsive to an activation of the light detector means by the air refracted in the output line.

5. The volumetric pump of claim 2 additionally including means for detecting the pumping of the preselected volume of fluid in accordance with the count of the incremental operations of the stepper motor and means responsive to such detection for providing a pumping of the fluid at a preselected low rate to maintain fluid communication between the patient and the source.

6. The volumetric pump of claim 1 additionally including adjustable means for providing for an adjustment in the incremental rate of operation of the stepper motor and means responsive to adjustments in the adjustable means for instantaneously adjusting the incremental rate of operation of the stepper motor in accordance with such adjustments.

7. The volumetric pump of claim 6 additionally including means coupled to the control means for counting the incremental operations of the stepper motor during each movement of the plunger in the first direction and for adjusting the rate of incremental operation of the stepper motor in driving the plunger in the second direction, during the next movement of the plunger in the second direction, to compensate for the time lost in driving the plunger in the first direction and to maintain the rate of transfer of the fluid between the patient and the source at the preselected controlled rate.

8. The volumetric pump of claim 1 wherein the control means are operative to produce a pulse drive stepping signal at a particular rate directly related to the preselected controlled rate and wherein the stepper motor is responsive on an incremental basis to each pulse drive stepping signal from the control means to drive the plunger on an incremental basis.

9. The volumetric pump of claim 1 additionally including means responsive to the pulse drive stepping signal during the operation of the stepper motor in driving the plunger in the first direction for accumulating such stepping signals during each movement of the plunger in the first direction and for introducing such additional pulse drive stepping signals to the stepper motor during the next movement of the plunger in the second direction to compensate for the failure of the pump to pump fluid during the operation of the plunger driving means in driving the plunger in the first direction.

10. The volumetric pump of claim 8 additionally including means for comparing the rate of the pulse drive stepping signal with the incremental operation of the stepper motor to monitor the proper operation of the stepper motor in accordance with the rate of the pulse drive stepping signals and means for stopping the operation of the stepper motor when the operation of the stepper motor is not in accordance with the rate of the pulse drive stepping signal.

11. The volumetric pump of claim 1 wherein the volumetric means is a disposable cassette and the plunger is disposed in the cassette and wherein means are included for retaining the cassette in position for pumping fluid and for providing for a quick removal of the cassette from the pump for a replacement of the cassette and wherein means are also included for providing a quick disconnect of the plunger driving mechanism from the plunger.

12. The volumetric pump of claim 11 wherein the additional means includes at least a pair of pins in one of the cassette and the pump to engage a complementary pair of openings in the other one of the cassette and the pump to snap the cassette in position into a particular relationship with the pump.

13. The volumetric of claim 11 wherein the volumetric cassette includes a valve mechanism movable between first and second positions and operative in the first position to provide for the flow of fluid between the pump and one of the patient and the source and operative in the second position to provide for the flow of fluid between the pump and the other one of the patient and the source.

14. The volumetric pump of claim 13 including valve position detector means to detect the positioning of the valve mechanism in the individual ones of the first and second positions and coupled to the control means to control the operation of the plunger driving means in the individual ones of the first and second positions in driving the plunger in the respective ones of the first and secnd directions.

15. The volumetric pump of claim 14 additionally including detector means for detecting the movement of the plunger to limit positions in the chamber during the movements of the plunger in the first and second directions and means responsive to such detections for interrupting the stepper motor in driving the plunger in the direction represented by such detections and for reversing the operation of the stepper motor.

16. A volumetric pump for pumping fluid from a source to an output line using a volumetric cassette for receiving fluid from the source and providing fluid to the output line where the cassette includes a chamber of a predetermined volume which is a fraction of volume of fluid in the source and also a fraction of the volume of the fluid to be pumped from the source and where the cassette also includes a plunger movable within the chamber for filling the chamber during movement of the plunger in a first direction and emptying the chamber during movement of the plunger in a second direction opposite to the first direction, including a stepper motor constructed to be operated in increments each representing a particular distance,
plunger driving means, including the stepper motor, operatively coupled to the plunger in the cassette for alternately driving the plunger in the first and second directions through the particular increments of distance,
control means coupled to the plunger driving means to control the plunger driving mechanism, with the control means including
first means for producing the incremental operation of the stepper motor at a controlled rate to obtain incremental movements of the plunger in each of the first and second directions,
second means for monitoring the count of the incremental operations of the stepper motor in driving the plunger in the second direction to control the volume of fluid pumped from the cassette chamber,
the second means including third means operative to preselect a digital count representating a particular amount of fluid to be transferred from the source to the output line,
the second means further including fourth means for counting the increments in the operation of the stepper motor in driving the plunger in the second direction, and
the second means further including fifth means operatively coupled to the third means and the fourth means for interrupting the operation of the stepper motor when the count in the fourth means corresponds to the count in the third means.

17. The volumetric pump of claim 16 wherein an output line extends from the cassette chamber and wherein means are included to detect air in the output line from the cassette and to activate an alarm upon such detection and wherein means are responsive to the detection of air in the output line for stopping the pumping of fluid from the cassette.

18. The volumetric pump of claim 17 wherein the means to detect the air in the output line from the cassette includes a light emitter to direct light toward the output line from the cassette and a light detector responsive to refracted light passing from the output line to detect changes in the refracted light resulting from the presence of air in the output line.

19. The volumetric pump of claim 16 additionally including means responsive to the operation of the fifth means in detecting the correspondence in the counts in the third and fourth means for adjusting the control means to provide for an operation of the stepper motor at a preselected low predetermined rate to keep open the pumping of the fluid from the cassette chamber after the preselected volume of fluid has been pumped.

20. The volumetric pump of claim 16 additionally including adjustable means for providing for a preselection of a particular rate of pumping of fluid and means responsive to the preselected rate provided by the adjustable means for operating the plunger driving means on an incremental basis at such rate.

21. The volumetric pump of claim 20 additionally including means coupled to the control means for measuring the time of movement of the plunger in the first direction and means for adjusting the rate of incremental operation of the plunger driving means in the second direction to compensate for the time of movement of the plunger in the first direction.

22. The volumetric pump of claim 16
wherein the stepper motor is operative on an incremental basis in driving the plunger in the first direction and wherein sixth means are operative to add to the preselected count in the third means the increments of operation of the stepper motor in driving the plunger in the first direction and wherein the fourth means is operative to count the increments in the operation of the stepper motor in driving the plunger in the first direction and wherein the fifth means is operative to interrupt the transfer of fluid from the source to the output line when the count from the fourth means corresponds to the adjusted count provided by the sixth means.

23. The volumetric pump of claim 16 wherein the control means produces a pulse drive stepping signal and the plunger driving mechanism includes a stepping motor responsive to the pulse drive stepping signal to drive the plunger on an incremental basis in the second direction.

24. The volumetric pump of claim 16 additionally including means for detecting the movements of the plunger to limit positions in the first and second directions and means responsive to the detection of the movements of the plunger to the limit positions for interrupting the operation of the plunger driving means in driving the plunger in the direction represented by the limit position detected.

25. In apparatus for use in a pump for pumping fluid from a source through a cassette and to an output line at a preselected controlled rate on an incremental basis until a preselected volume of fluid has been pumped where the pump includes a stepper motor and a driving mechanism operative by the stepper motor for controlling the filling of the cassette and for controlling at least partial emptying of the cassette on the incremental basis at the controlled rate and the driving mechanism includes a shuttle and where the pump further includes a valve control mechanism having first and second states of operation for controlling the supply of fluid from the source to the cassette in the first state of operation and the flow of fluid from the cassette to the output line in the second state of operation and further includes detent means, the cassette including
- a unitary housing constructed to be handled manually for coupling to the driving mechanism and the valve control mechanism,
- a chamber fixedly disposed on the housing and provided with a predetermined volume per unit of length which predetermined volume is a small fraction of the fluid in the source and a fraction of the fluid to be transferred between the source and the individual,
- a plunger movable linearly and incrementally within the chamber in first and second opposite directions for coupling to the driving mechanism in the pump in accordance with the manual positioning of the housing for at least partially filling the chamber with the fluid during the linear and incremental movement of the plunger in the first direction and for at least partially emptying the chamber of a predetermined amount of the fluid upon each linear and incremental movement of the plunger in the second direction,
- the plunger including means for engaging the shuttle on the pump to provide for a linear and incremental movement of the plunger in the first and second opposite directions by the driving mechanism,
- first and second lines fixedly disposed on the housing in communication with the chamber, the first line also being disposed for communication with the source in the first state of operation of the valve control mechanism and the second line also being disposed for communication with the output line in the second state of operation of the valve control mechanism,
- a valve mechanism constructed to cooperate with the valve control mechanism in providing the first and second states of operation and fixedly disposed on the housing between the first and second lines and in communication with the first and second lines and the chamber for coupling to the valve control mechanism in accordance with the manual positioning of the housing for providing for the flow of fluid from the chamber to the source and preventing the coupling of the chamber to the output line in the first state of operation of the valve control mechanism and for coupling the chamber to the output line and preventing the coupling of the chamber to the source in the second state of operation of the valve control mechanism, and
- detent means included in the cassette for engaging the detent means in the pump to couple the cassette to the pump in a particular relationship in accordance with the manual positioning of the housing in fixed relationship to the pump means to obtain the pumping of fluid by the pump through the cassette.

26. In apparatus as set forth in claim 25 where the detent means on the pump includes a pair of spaced pins, the detent means in the cassette including a pair of holes for receiving the pins.

27. A volumetric pump for pumping fluid from a source to an output line at a preselected controlled rate until a preselected volume of fluid has been pumped, including
  volumetric means for receiving fluid from the source of fluid and providing fluid to the output line, and including
  a chamber in the volumetric means of a predetermined volume per unit of length, which predetermined volume is a fraction of the volume of fluid in the source and a fraction of the fluid to be pumped to the output line,
  a plunger movable within the chamber in a first direction for filling the chamber with fluid and movable in the chamber in a second direction opposite to the first direction for at least partially emptying the chamber,
  a plunger driving mechanism coupled to the plunger for driving the plunger in the first direction to fill and in the second direction at least partially empty the chamber,
  the plunger driving mechanism including
  a stepper motor constructed to provide movements on an incremental basis in first and second opposite directions where each incremental movement constitutes a particular distance, the stepper motor being operatively coupled to the plunger driving mechanism to drive the plunger driving mechanism in the first and second directions through the incremental distances in accordance with the incremental operation of the stepper motor in the first and second directions,
  control means coupled to the stepper motor for controlling the operation of the stepper motor and including
  first means for obtaining an operation of the stepper motor at a controlled rate on an incremental basis in the second direction to at least partially empty the chamber by a predetermined volume at a preselected rate until the chamber is at least partially empty and for obtaining the operation of the stepper motor on an incremental basis in the first direction to refill the cassette, and second means for monitoring the operation of the stepper motor in the second direction to count the number of incremental operations of the stepper motor in the second direction and thereby to determine the volume of fluid pumped from the cassette, third means adjustable to provide a count representative of a preselected volume of fluid, fourth means including a first diagnostic alarm coupled to the second means and the third means for providing an alarm when the count indicated by the second means to represent the volume of fluid corresponds to the count in the third means to represent the preselected volume of fluid, and fifth means including a second diagnostic alarm for monitoring the plunger driving mechanism for detecting the driving of the plunger in the second direction on an incremental basis at a rate less than the preselected rate and for providing an alarm upon such detection.

28. The volumetric pump of claim 27 wherein a fluid line is provided between the source and the volume means and the fifth means is constructed to provide an alarm upon an occulsion of the fluid line or the output line from the volume means.

29. The volumetric pump of claim 27 additionally including means responsive to the provision of the alarm by the fourth means for adjusting the control means to obtain an operation of the stepper motor at a low predetermined rate of pumping to maintain the pumping through the output line after the preselected volume has been pumped.

30. A battery operated volumetric pump for pumping fluid dispensed from a source of fluid to an output line at a preselected controlled rate, including a battery, a volumetric cassette for receiving fluid from the source of fluid and providing fluid to the output line, and including a chamber of a predetermined volume per unit of length and with a total volume which is a fraction of the source of fluid and a fraction of the volume of fluid to be dispensed from the source, the cassette also including a plunger movable within the chamber for filling and at least partially emptying the chamber a predetermined amount upon movement of the plunger in alternate directions, and a stepper motor constructed to operate in first and second opposite directions in increments each representing a particular distance, the stepper motor being operatively coupled to the battery to be energized by the battery, a plunger driving mechanism, including the stepper motor, coupled to the plunger for driving the plunger on an incremental basis in alternate directions to fill and at least partially empty the chamber, control means coupled to the plunger driving mechanism for controlling the operation of the stepper motor to alternately drive the plunger on an incremental basis at a controlled speed in one direction to at least partially empty the cassette chamber a predetermined amount at a preselected rate until the chamber is at least empty and to drive the plunger on an incremental basis in the opposite direction to refill the cassette, detector means coupled to the battery for detecting the voltage level across the battery, and an alarm mechanism coupled to the detector means for actuating an alarm upon the detection of a voltage level of the battery below a preselected value.

31. The volumetric pump of claim 30 additionally including means for preselecting a rate of incremental operation of the stepper motor in the first direction and means coupled to the control means for counting the number of increments of operation of the stepper motor in the direction for refilling the cassette chamber during each operation of the stepper motor in that direction and for adjusting the rate of the incremental operation of the stepper motor in the first direction, during the next operation of the stepper motor in that direction, to empty the cassette chamber at a rate higher than the rate preselected for the incremental operation of the stepper motor in that direction to compensate for the time lost in refilling the cassette chamber.

32. A volumetric pump for pumping fluid dispensed from a source of fluid to an output line at a preselected controlled rate until a preselected volume of fluid has been pumped, including a volumetric cassette for receiving fluid from the source of fluid and providing fluid to the output line, and including a chamber of a predetermined volume per unit of length and with a total volume which is a fraction of the source of fluid and a fraction of the volume of fluid to be dispensed to the output line, the cassette also including a plunger movable within the chamber in a first direction for filling the chamber with fluid and movable within the chamber in an opposite direction for at least partially emptying the chamber of the fluid, a stepper motor constructed to operate on an incremental basis in first and second opposite directions where each increment represents a particular displacement a plunger driving mechanism, including the stepping motor, coupled to the plunger for driving the plunger on an incremental basis in alternate directions in accordance with a pulse drive stepping signal to fill and at least partially empty the chamber and wherein a predetermined number of incremental operations of the stepper motor equal a unit quantity of fluid pumped and the rate of the fluid pumped is in accordance with the rate of introduction of the pulse drive stepping signal, means for adjusting the rate of the pulse drive stepping signal in accordance with the preselected controlled rate, control means coupled to the plunger driving mechanism for providing a pulse drive stepping signal at a particular rate for controlling the plunger driving mechanism to alternately drive the plunger on an incremental basis in the first direction at a controlled speed in accordance with the rate of the pulse drive stepping signal to at least partially empty the cassette chamber a predetermined amount at a preselected rate and to drive the plunger on an incremental basis in the opposite direction to refill the cassette, means for providing a preselected count of the number of increments of operation of the stepper motor in the opposite direction, means operatively coupled to the stepper motor for counting the number of incremental operations of the stepper motor in the opposite direction, and means operatively coupled to the last two mentioned means for comparing the count in the last two mentioned means to interrupt the operation of the stepper motor when the counts coincide.

33. The volumetric pump of claim 32 additionally including means responsive to the pulse drive stepping signal during each refilling of the cassette chamber for counting the number of the pulse drive stepping signal during each such refilling and means responsive to such count for changing the preselected count in accordance with such count.

34. The volumetric pump of claim 32 additionally includes means responsive to the pulse drive stepping signal during each refilling of the cassette chamber for counting the number of the pulse drive stepping signal during each such refilling and for providing an additional count in the pulse drive stepping signal corresponding to such count during the next operation of the stepper motor in the opposite direction for compensating the rate of pumping the fluid to the output line to equal the preselected rate.

35. The volumetric pump of claim 32 additionally including means for comparing the rate of the pulse drive stepping signal with the rate of incremental operation of the stepper motor to monitor the incremental operation of the stepper motor in accordance with the pulse drive stepping signal and including means responsive to such comparison for interrupting the incremental operation of the pump at the preselected controlled rate when the incremental operation of the stepper motor is not in accordance with the rate of the pulse drive stepping signal.

36. A volumetric pump for pumping fluid dispensed from a source of fluid to an output line at a preselected controlled rate including a volumetric cassette for receiving fluid from the source of fluid and providing fluid to the output line, and including a chamber of a predetermined volume per unit of length and of a total volume which is a fraction of the source of fluid and a fraction of the fluid to be dispensed to the output line, the cassette also including a plunger movable in a first direction within the chamber for filling the chamber with the fluid and also movable within the chamber in an opposite direction for at least partially emptying the chamber of the fluid, a plunger driving mechanism coupled to the plunger for alternately driving the plunger in the first and opposite directions respectively to fill and at least partially empty the chamber, and the plunger driving mechanism including a stepper motor constructed to operate on an incremental basis in first and second opposite directions to provide particular incremental displacements in such directions in accordance with the incremental operations of the stepper motor, a valve mechanism to control the flow of fluid to and from the cassette chamber during filling and at least partial emptying of the cassette chamber, the valve mechanism having first and second positions and being synchronized in operation between the first and second positions in accordance with the operation of the stepper motor to provide for a flow of fluid to the chamber during the incremental operation of the stepper motor in driving the plunger in the first direction and to provide for a flow of fluid from the chamber during the incremental operation of the stepper motor in driving the plunger in the second direction, and control means coupled to the plunger driving mechanism to control the stepper motor to alternately drive the plunger at a controlled rate in the second direction, with the valve mechanism in the first position, to at least partially empty the cassette chamber at a preselected rate until the chamber is at least partially empty, and to drive the plunger in the first direction, with the valve mechanism in the second position, to refill the cassette.

37. The volumetric pump of claim 36 additionally including valve position detector means included in the control means to control the direction of movement of the plunger driving mechanism and to control the movement of the valve mechanism between the first and second positions.

38. The volumetric pump of claim 37 additionally including means operatively coupled to the stepper motor for counting the incremental operations of the stepper motor in driving the plunger in the first direction during each movement of the plunger in the first direction and means operatively coupled to the stepper motor for increasing the incremental operation of the stepper motor, during the next operation of the stepper motor in driving the plunger in the second direction, by a count corresponding to the count of the incremental operations of the stepper motor in driving the plunger in the first direction during the previous movement of the plunger in the first direction.

39. Apparatus for use in a pump for pumping fluid between a source and an individual at a controlled rate where the pump includes a stepper motor and first means operatively coupled to the stepper motor for moving linearly and incrementally and for pumping fluid in accordance with such linear and incremental movement and includes a shuttle on the first means and where the pump further includes second means for controlling the pumping of the fluid between the source and the individual and having first and second states of operation and further includes third means for providing detents, such apparatus including, a hollow chamber having a particular volume per unit of length and having first and second conduits and having a volume considerable less than the volume of fluid to be transferred between the source and the individual, the chamber being disposed to provide for the passage of fluid between the source and the chamber through the first conduit and to provide for the passage of such fluid between the chamber and the individual through the second conduit, the chamber and the first and second conduits being disposed and constructed to provide for the passage of the fluid between the source and the chamber and between the chamber and the individual without contacting the pump or the first means or the second means, a plunger disposed in the chamber for coupling to the first means in a particular relationship for linear and incremental movement by the first means in a first direction to provide for the passage of the fluid through the first conduit between the chamber and the source and for linear and incremental movement in a second direction opposite to the first direction to provide for the passage of the fluid between the chamber and the individual, the plunger means being constructed to be engaged by the shuttle on the first means in the pump to provide for a positive drive of the plunger by the first means, a valve disposed in communication with the chamber and in fixed relationship with the chamber and in communication with the first and second conduits for coupling to the second means in a particular relationship and cooperative with the second means in the coupled relationship for providing the first and second states of operation to provide for a flow of the fluid between the source and the chamber through the first conduit and to prevent the flow of fluid between the chamber and the individual through the second conduit in the first state of operation of the second means and to provide for a flow of the fluid between the chamber and the individual through the second conduit and to prevent the flow of the fluid between the source and the chamber through the first conduit in the second state of operation of the second means, and coupling means disposed in fixed relationship with the chamber for fixed coupling to the third means in the pump to provide for a coupling of the plunger to the first means and a coupling of the valve to the second means and thereby to provide for a controlled transfer of the fluid between the source and the individual in accordance with the operation of the second means in the first and second states.

40. The combination set forth in claim 39 wherein the coupling means includes means operatively coupled to the chamber to provide for a particular coupling between the valve and the second means in the pump to provide for a controlled operation of the valve between the first and second positions by the second means.

41. The combination set forth in claim 39 wherein the coupling means includes means operatively coupled to the chamber to provide for a particular coupling between the plunger and the first means in the pump to provide for an operation of the plunger by the first means.

42. The combination set forth in claim 41 wherein the coupling means includes detent means provided on the pump and detent means operatively coupled to the chamber to cooperate with detent means on the pump to provide for a quick coupling of the chamber to the pump in fixed disposition on the pump and to provide for a quick disconnect of the chamber from the pump.

43. In combination for pumping fluid between a source and an individual, drive means including a linearly reciprocatable drive member, the reciprocatable drive member including a shuttle, pump means operable to reciprocate the drive member on a controlled basis in the linear direction, the pump means being constructed to provide an incremental movement of the drive member in the linearly reciprocal directions with each increment representing a movement of the drive member through a particular increment of distance, the pump means including a stepper motor responsive to the introduction of pulses to provide precise increments of movement in accordance with the introduction of the pulses, a hollow chamber having a particular volume per unit of length and having a total volume considerably less than the volume of fluid to be transferred between the source and the individual and having first and second conduits, the chamber being disposed to provide for the passage of fluid between the source and the chamber through the first conduit and to provide for the passage of fluid between the chamber and the individual through the second conduit, a plunger disposed in the chamber for linearly reciprocating movement with the drive member on an incremental basis in a first direction to provide for the passage of the fluid through the first conduit between the chamber and the source and for linearly reciprocating movement on an incremental basis in a second direction opposite to the first direction to provide for the passage of the fluid between the chamber and the individual, the plunger including a portion for positively engaging the shuttle, valve control means fixedly disposed in communication with the chamber and the first and second conduits and having first and second states of operation and operable in the first state to provide for a flow of fluid between the source and the chamber through the first conduit and to prevent the flow of the fluid between the chamber and the individual through the second conduit and operable in the second state to provide for the flow of fluid between the chamber and the individual through the second conduit and to prevent the flow of the fluid between the source and the chamber through the first conduit, means responsive to the operation of the valve control means in individual ones of first and second states for providing an operation of the valve control means in the other one of the first and second states, the hollow chamber and the plunger being physically displaced from the drive member, the pump means and the valve control means to provide for the pumping of the fluid through the chamber and the first and second conduits between the source and the individual without contacting the drive member, the pump means and the valve control means, pulse means for providing a plurality of pulses at a variably controlled rate, the pulse means being means operatively coupled to the stepper motor to provide an incremental operation of the stepper motor at the variably controlled rate in driving the drive member in the linearly reciprocating directions through a plurality of cycles to provide for the flow of fluid into and out of the chamber at a particular rate related to the variably controlled rate of incremental operation of the stepper motor, first adjustable means for preselecting a particular number of increments of movement of the plunger in a particular one of the linearly reciprocatable directions to control the amount of fluid to be transferred between the source and the individual, counting means operatively coupled to the pump means for counting the number of increments of movement of the plunger in the particular one of the linearly reciprocatable directions to determine the incremental flow of fluid through the chamber at the variably controlled rate, and means operatively coupled to the adjustable means and the counting means for interrupting the incremental operation of the stepper motor at the variably controlled rate to interrupt the flow of fluid through the chamber at the particular rate when the count provided by the counting means corresponds to the preselected amount selected by the adjustable means.

44. The combination set forth in claim 43, including, means responsive to the movement of the drive member in the other one of the reciprocating directions for counting the number of incremental movements of the drive member in this direction, and means responsive to the count provided by the last mentioned means for adjusting the rate of incremental operation of the pump means in driving the drive member in the particular direction to compensate for the movement of the drive member in the other one of the reciprocating directions.

45. The combination set forth in claim 43, including, means responsive to the cumulative transfer of the preselected amount of the fluid out of the chamber for thereafter lowering the rate of transfer of fluid out of the chamber to a particular minimum level to maintain a communication between the source and the individual.

46. The combination set forth in claim 43, including, means operatively coupled to a particular one of the first and second conduits for determining whether only the fluid is passing at each instant through the particular conduit, and means responsive to the determination provided by the last mentioned means for instantaneously interrupting the flow of fluid through the particular conduit when the last mentioned means determines at any instant that only the fluid is not passing through the particular conduit.

47. The combination set forth in claim 43, including, means operatively coupled to the stepper motor for determining whether the stepper motor is operating on an incremental basis at a particular rate, and means responsive to the determination provided by the last mentioned means for interrupting the operation of the stepper motor when the stepper motor is operating on an incremental basis at a rate lower than the particular rate.

48. The combination set forth in claim 45 wherein the pump includes a stepping motor operative on an incremental basis to drive the driving member on an incremental basis to obtain the pumping of a particular amount of fluid in each such increment and wherein means are responsive to a movement of the driving member in the other one of the reciprocating directions for determining the number of increments in the operation of the stepping motor during such reciprocating movement and wherein means are responsive to the determination provided by the last mentioned means for compensating, in accordance with such determination, in the rate of the incremental operation of the motor in driving the drive member in the particular one of the reciprocating directions.

49. In combination in a cassette for use with a pump for passing fluid at a controlled rate between a source and an individual where the pump includes first means including a stepper motor of a first particular configuration and constructed to provide a flow of the fluid on an incremental basis at a particular rate and including a shuttle movable by the stepper means and includes second means of a second particular configuration and constructed to control the direction of fluid flow and detent means having a third particular configuration and constructed to provide a mating relationship, a hollow chamber constructucted to provide a storage of limited volume relative to the volume of fluid to be transfused between the source and the individual and having first and second conduits respectively disposed for communication with the source and the individual and having a particular volume per unit of length, a plunger movable within the chamber in opposite reciprocatory directions in sequence for an insertion of the fluid into the chamber during a movement of the plunger in one of the opposite reciprocatory directions in the sequence and to provide for a transfer of fluid from the chamber during a movement of the plunger in the other one of the opposite reciprocating directions in the sequence, the plunger including means engaging the shuttle on the basis of a quick connect and disconnect for movement by the shuttle, the plunger including means having a configuration corresponding to the configuration of the shuttle to provide a mating relationship with the shuttle for a movement on an incremental basis of the plunger in opposite reciprocating directions by the first means, a valve movable between first and second positions and operable in the first position to provide a communication between the source and the chamber through the first conduit and to prevent a communication between the chamber and the individual and operable in the second position to provide a communication between the chamber and the individual through the second conduit and to prevent a communication between the source and the chamber, means having a configuration corresponding to the second particular configuration to provide a mating relationship between the means and the valve for an operation of the valve on a controlled basis between the first and second positions, and means having a configuration corresponding to the third particular configuration to mate with the detent means on the basis of a quick connect and disconnect to provide a fixed disposition of the chamber and the plunger and valve relative to the pump.

50. The combination set forth in claim 49 wherein the detent means constitutes a pair of spaced pins on the pump and a pair of spaced holes in the cassette to receive the pair of spaced pins.

51. The combination set forth in claim 49 wherein the second means includes a shaft rotatable between first and second positions and wherein the valve engages the shaft and has a portion rotatable between the first and second positions to control the communication between the source and the chamber and between the chamber and the individual.

52. The combination recited in claim 43, including, the counting means including means responsive to the operation of the stepper motor in driving the drive member in the other one of the reciprocating directions for counting the number of incremental operations of the stepper motor in such other one of the reciprocal directions in each such movement of the drive member, means responsive to the count provided by the last mentioned means for adding such count to the preselected count provided by the adjustable means, and means responsive to the count representing the number of incremental operations of the stepper motor in driving the drive member in the other one of the reciprocal directions in each such movement of the drive member for increasing the incremental operations of the stepper motor in driving the drive member in the particular direction in the next movement of the drive member in the particular direction.

53. In apparatus as set forth in claim 25, the chamber being provided with a relatively short length in the direction of movement of the plunger in comparison to the width of the chamber and the chamber being provided with a substantially constant cross sectional area in the direction of its width at the different positions along the length of the chamber.

54. In apparatus as set forth in claim 25 where the pump has detent means disposed in a first direction transverse to the direction of movement of the plunger and spaced from each other in a second direction transverse to the direction of movement of the plunger, the cassette having detent means for cooperation with the detent means in the pump and the plunger including means for coupling to the driving mechanism in a direction transverse to the direction of movement of the plunger.

55. In apparatus as set forth in claim 54 where the detent means in the pump constitutes a pair of spaced pins, the detent means in the cassette constituting a pair of holes for receiving the pins.

56. In apparatus as set forth in claim 55, the chamber being provided with a relatively short length in the direction of movement of the plunger in comparison to the width of the chamber and the chamber being provided with a substantially constant cross sectional area in the direction of its width at different positions along the length of the chamber.

57. The volumetric pump set forth in claim 27 wherein sixth means are operative to detect the time for the operation of the plunger driving mechanism in driving the plunger in the dirst direction and seventh means responsive to the time detected by the third means for adjusting the preselected volume of fluid represented by the third means in accordance with such time detection.

58. The volumetric pump set forth in claim 27 wherein sixth means are operative to detect the time for the plunger driving mechanism in driving the plunger in the first direction and seventh means are operative for adjusting the operation of the first means to vary the rate of incremental movement of the plunger in the second direction in accordance with such time detection.

59. The combination recited in claim 1, including, means responsive to the operation of the plunger driving means in driving the plunger in the first direction for counting such increments in the operation of the plunger driving means, means responsive to the count of the increments from the last mentioned means for adding such count to the preselected count, and means for interrupting the operation of the plunger driving means when the count of the increments in the operation of the plunger driving means corresponds to the count from the last mentioned means.

60. In the apparatus set forth in claim 25, the valve control mechanism being rotatable between first and second positions and being operable in the first state in the first position and being operable in the second state in the second position.

61. Apparatus as set forth in claim 39 wherein the valve is rotatable between first and second positions and is operable in the first state in the first position and is operable in the second state in the second position and the second means in the pump includes a valve motor shaft rotatable between first and second positions and the valve includes a valve portion for positively engaging the valve motor shaft for rotation with the valve motor shaft when the coupling means engages the third means in the pump and the stepper motor is constructed to provide the incremental operation on an open loop basis.

62. In the combination set forth in claim 43, the valve being rotatable between first and second positions and being operable in the first state in the first position and being operable in the second state in the second position and the valve control means including a valve motor shaft rotatable between first and second positions and the stepper motor being constructed to provide the incremental operation on an open loop basis.

* * * * *